United States Patent
Chen et al.

(10) Patent No.: US 10,117,890 B2
(45) Date of Patent: Nov. 6, 2018

(54) METHODS AND COMPOSITIONS FOR TREATING PAIN

(71) Applicant: Academia Sinica, Taipei (TW)

(72) Inventors: Chih-Cheng Chen, Taipei (TW); Yun-Lian Lin, Taipei (TW); Jim-Min Fang, Taipei (TW); Yijuang Chern, Taipei (TW); Chia-Ching John Lin, Kaohsiung (TW); Wei-Nan Chen, Keelung (TW); Chun-Jung Lin, Taipei (TW)

(73) Assignee: Academia Sinica, Taipei (TW)

(*) Notice: Subject to any disclaimer, the term of this patent is extended or adjusted under 35 U.S.C. 154(b) by 0 days.

(21) Appl. No.: 15/376,281

(22) Filed: Dec. 12, 2016

(65) Prior Publication Data

US 2017/0224716 A1 Aug. 10, 2017

Related U.S. Application Data

(63) Continuation of application No. 14/378,013, filed as application No. PCT/US2013/025580 on Feb. 11, 2013, now abandoned.

(60) Provisional application No. 61/597,742, filed on Feb. 11, 2012.

(51) Int. Cl.
| | | |
|---|---|---|
| *A01N 43/04* | (2006.01) | |
| *A61K 31/70* | (2006.01) | |
| *A61K 31/7076* | (2006.01) | |
| *A61K 36/8988* | (2006.01) | |
| *A61K 45/06* | (2006.01) | |

(52) U.S. Cl.
CPC ...... *A61K 31/7076* (2013.01); *A61K 36/8988* (2013.01); *A61K 45/06* (2013.01)

(58) Field of Classification Search
CPC .............. A61K 45/06; A61K 31/7076; A61K 36/8988; A61K 2300/00
See application file for complete search history.

(56) References Cited

U.S. PATENT DOCUMENTS

| | | | | | |
|---|---|---|---|---|---|
| 5,677,290 | A * | 10/1997 | Fukunaga | ............. | A61K 31/00 514/46 |
| 5,679,649 | A * | 10/1997 | Fukunaga | ............. | A61K 31/00 514/46 |
| 5,679,650 | A * | 10/1997 | Fukunaga | ............. | A61K 31/70 514/221 |
| 5,691,318 | A * | 11/1997 | Sollevi | ............. | A61K 31/7076 514/46 |
| 5,942,497 | A * | 8/1999 | Fukunaga | ............. | A61K 31/70 514/221 |
| 6,004,945 | A * | 12/1999 | Fukunaga | ............. | A61K 31/00 514/46 |
| 6,180,616 | B1 * | 1/2001 | Fukunaga | ............. | A61K 31/00 514/46 |
| 6,642,209 | B1 * | 11/2003 | Fukunaga | ............. | A61K 31/00 514/45 |
| 7,351,434 | B2 * | 4/2008 | Chern | ............. | A61K 31/421 424/725 |
| 7,807,685 | B2 * | 10/2010 | Higginbottom | ........ | C07H 19/16 514/263.23 |
| 7,825,102 | B2 * | 11/2010 | Fishman | ............. | A61K 31/52 514/46 |
| 8,129,357 | B2 * | 3/2012 | Chern | ............. | A61K 31/7076 424/725 |
| 9,132,131 | B2 * | 9/2015 | Salvemini | .......... | A61K 31/7076 |
| 2003/0096788 | A1 * | 5/2003 | Bays | ............. | C07H 19/16 514/46 |
| 2008/0176816 | A1 | 7/2008 | Chern et al. | | |
| 2009/0181920 | A1 * | 7/2009 | Watkins | ............. | A61K 31/7076 514/45 |
| 2012/0295863 | A1 | 11/2012 | Lin et al. | | |
| 2013/0045942 | A1 | 2/2013 | Shi et al. | | |
| 2015/0038445 | A1 | 2/2015 | Chen et al. | | |

FOREIGN PATENT DOCUMENTS

| | | | |
|---|---|---|---|
| WO | WO 98/01459 | A1 | 1/1998 |
| WO | WO 98/58653 | A1 * | 12/1998 |
| WO | WO 2009/089425 | A1 * | 7/2009 |

OTHER PUBLICATIONS

Sawynok et al., "Involvement of Mast Cells, Sensory Afferents, and Sympathetic Mechanisms in Paw Edema Induced by Adenosine A(1) and A(2B/3) Receptor Agonists," European Journal of Pharmacology, 395(1), 47-50 (2000).*

(Continued)

*Primary Examiner* — Lawrence E Crane
(74) *Attorney, Agent, or Firm* — Wolf, Greenfield & Sacks, P.C.

(57) ABSTRACT

Methods for treating pain such as fibromyalgia, comprising administering to a subject in need thereof an effective amount of an adenosine analog, wherein the adenosine analog may be a compound of Formula (I):

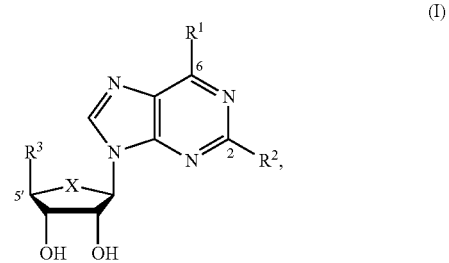

(I), or a pharmaceutically acceptable salt thereof. Pharmaceutical compositions comprising the adenosine analog for use in treating pain (e.g., fibromyalgia), optionally further comprising Substance P (SP), are also provided.

8 Claims, 9 Drawing Sheets

(56) References Cited

OTHER PUBLICATIONS

Fliri et al., "Drug Effects Viewed for a Signal Transduction Network Perspective," Journal of Medicinal Chemistry, 52(24), 8038-8046 (2009.*
Lin et al., "An Antinociceptive Role fopr Substance P in Acid-Induced Chronic Muscle Pain," Proc. Natl. Acad. Science USA, 109(2), E76-E83 (Epub Nov. 14, 2011); copy supplied by applicant in parent case.*
Brederson et al., "Fibromyalgia: Mechanisms, Current Treatment and Animal Models," Current Pharmaceutical Biotechnology, 12, 1613-1626 (2011); copy supplied by applicant, see 1.132 declaration.*
De Felipe et al., Altered nociception, analgesia and aggression in mice lacking the receptor for substance P.Nature. Mar. 26, 1998;392(6674):394-7.
Delumeau et al., Synergistic Regulation of Cytosolic Ca2+ Concentration in Mouse Astrocytes by NK1 Tachykinin and Adenosine Agonists, Journal of Neurochemistry, 1991, vol. 57, No. 6, pp. 2026-2035.
Fredholm et al., International Union of Basic and Clinical Pharmacology. LXXXI. Nomenclature and classification of adenosine receptors—an update. Pharmacol Rev. Mar. 2011;63(1):1-34. doi:10.1124/pr.110.003285. Epub Feb. 8, 2011.
Poon et al., Antinociception by adenosine analogs and an adenosine kinase inhibitor: dependence on formalin concentration. Eur J Pharmacol. Nov. 14, 1995;286(2):177-84.

* cited by examiner

METHODS AND COMPOSITIONS FOR TREATING PAIN

CROSS-REFERENCE TO RELATED APPLICATIONS

This application is a continuation application of U.S. application Ser. No. 14/378,013 filed Aug. 11, 2014, now abandoned, which is the National Stage of International Application No. PCT/US2013/025580 filed Feb. 11, 2013, which claims priority to U.S. provisional application under Ser. No. 61/597,742, filed on Feb. 11, 2012. The content of each of the prior applications is herein incorporated by reference in its entirety.

BACKGROUND OF THE INVENTION

The present invention is directed to medical methods and compositions for treatment of pain, in particularly acid-induced pain.

Pain is an unpleasant sensory and emotional experience associated with actual or potential tissue damage, for example, which may result from damage to body tissue, for example in general medical illnesses, cancer, neuropathies, and perioperative conditions. Pain may also be associated with medical disorders without a known cause, such as migraine and psychosomatic illness.

It is known Substance P (SP) is an undecapeptide belonging to the tachykinin small peptide family. SP is a pain neurotransmitter that helps excite and transmit pain signals from neural cells in many organs. Substance P is an important element in pain perception. The sensory function of substance P is thought to be related to the transmission of pain information into the central nervous system. Substance P coexists with the excitatory neurotransmitter glutamate in primary afferents that respond to painful stimulation. (De Felipe et al., Altered nociception, analgesia and aggression in mice lacking the receptor for substance P. *Nature* 392 (6674): 394-397, March 1998.) High levels of SP in muscle tissues and spinal fluid are frequently associated with chronic muscle pain such as myofascial pain syndrome and fibromyalgia, but the role of SP in muscle pain transmission and perception was unclear.

It was disclosed by Lin et al. that SP is an antinociceptive role in acid-induced chronic muscle pain. Lin showed that a single i.m. acid injection in mice lacking SP signaling by deletion of the tachykinin precursor 1 (Tac1) gene or coadministration of NK1 receptor antagonists produced long-lasting hyperalgesia rather than the transient hyperalgesia seen in control animals, and the inhibitory effect of SP was found exclusively in neurons expressing acid-sensing ion channel 3, where SP enhanced M-channel-like potassium currents through the NK1 receptor in a G protein-independent but tyrosine kinase-dependent manner. Furthermore, the SP signaling could alter action potential thresholds and modulate the expression of TTX-resistant sodium currents in medium-sized muscle nociceptor. (Lin et al., An antinociceptive role for substance P in acid-induced chronic muscle pain. PNAS 109 (2): E76-E83, January 2012.)

It is still desirable to develop a method or pharmaceutical composition for treating or managing pain.

SUMMARY OF THE INVENTION

The present invention is based on the unexpected discovery that a number of adenosine analogs are effective for the treatment of pain through activation of neurokinin 1 (NK1) receptor signaling pathway in muscle nociceptors, thereby inducing the activation of activation of M-type potassium channel to induce outward currents.

In one aspect, the present invention provides a use in the manufacture of a medicament for treating pain of an adenosine analog that activates NK1 receptor signaling, thereby inducing outward current.

In certain embodiments of the invention, the pain is an acid-induced pain. In an example, the pain is an acid-induced muscle pain, particularly an acid-induced chronic muscle pain.

According to the invention, the pain may also be selected from the group consisting of inflammatory pain, cancer pain, chest pain, back pain, facial pain, joint pain, muscular pain syndromes, neuropathic pain, peripheral pain, cancer and tumor pain, sympathetic pain, postoperative pain, and post-traumatic pain.

In some certain examples of the invention, the pain may also be fibromyalgia, myofascial pain, bladder pain syndrome or pain caused by irritable bowel syndrome.

In one example of the invention, the adenosine analog is isolated from a *Gastrodia* extract.

In certain embodiments of the invention, the adenosine analog is a compound of Formula (I):

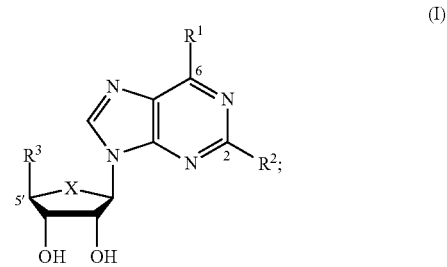

(I)

or a pharmaceutically acceptable salt thereof, wherein:

X is O, S or $CH_2$, $R^1$ is selected from the group consisting of $NHR^4$, $NH(CH_2)_n R^4$, $NH-NHR^4$, $NHCONHR^4$, $NH-OR^4$, $O-NHR^4$, and $SR^4$;

$R^2$ is selected from the group consisting of hydrogen (H), halogen, cyano, $OR^4$, $NHR^4$, substituted or unsubstituted alkyl, substituted or unsubstituted alkenyl, substituted or unsubstituted alkynyl, substituted or unsubstituted cycloalkyl, substituted or unsubstituted aryl (Ar), substituted or unsubstituted aralkyl, and a substituted or unsubstituted heterocyclyl;

$R^3$ is selected from the group consisting of halomethyl, hydroxymethyl ($HOCH_2$), alkoxymethyl ($R^4OCH_2$), azidomethyl ($N_3CH_2$), aminomethyl ($H_2NCH_2$), substituted or unsubstituted aminomethyl, amidomethyl ($H_2NCOCH_2$), sulfanylmethyl ($R^4S$), sulfonylmethyl ($R^4SO_2$), triazolylmethyl, cyanomethyl ($N\equiv CCH_2$), cyano, substituted or unsubstituted carbonyl ($R^4CO$), COOH, substituted or unsubstituted aminocarbonyl ($R^4HNCO$), substituted or unsubstituted alkynyl, and substituted or unsubstituted tetrazole;

n is 1, 2 or 3;

each instance of $R^4$ is independently selected from the group consisting of H, alkyl, cycloalkyl, substituted or unsubstituted Ar, substituted or unsubstituted aralkyl, and a substituted or unsubstituted heterocyclyl;

Ar is selected from the group consisting of substituted or unsubstituted phenyl, substituted or unsubstituted polyarene, and a substituted or unsubstituted heterocycle.

In some certain embodiments of the present invention, the adenosine analog is a compound of Formula (II):

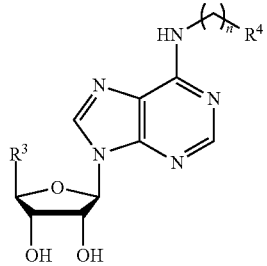

(II)

or a pharmaceutically acceptable salt thereof.

In one example of the compound of formula (II) according to the invention, the adenosine analog is $N^6$-(4-hydroxybenzyl)adenosine having the formula T1-11:

T1-11

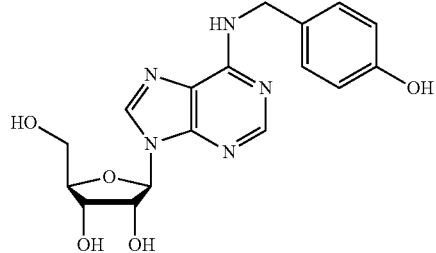

or a pharmaceutically acceptable salt thereof.

In another example of the compound of formula (II) according to the invention, the adenosine analog is a compound having the formula JMF1998:

JMF1998

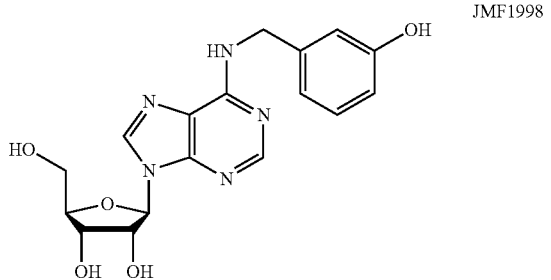

or a pharmaceutically acceptable salt thereof.

In a further example of the compound of formula (II) according to the invention, the adenosine analog is a compound having the formula JMF2665:

JMF2665

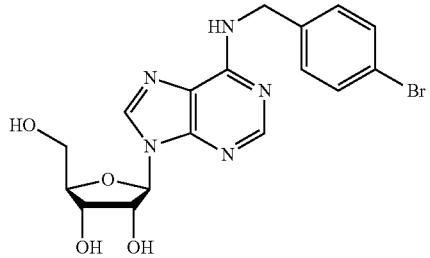

or a pharmaceutically acceptable salt thereof.

In other embodiments of the present invention, the adenosine analog is a compound of formula (III):

(III)

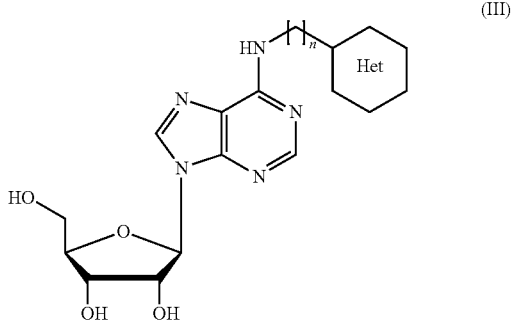

or a pharmaceutically acceptable salt thereof, wherein Het is a substituted or unsubstituted heterocycle comprising 5- or 6-membered ring or fused ring containing at least one nitrogen, oxygen or sulfur heteroatoms.

In preferred embodiments of the invention, Het is selected from the group consisting of pyrrole, furan, thiophene, pyridine, piperidine, piperazine, indole, benzofuran, benzothiophene, and quinoline.

In one example of the compound of formula (III) according to the invention, the adenosine analog is a compound having the formula JMF1907:

JMF1907

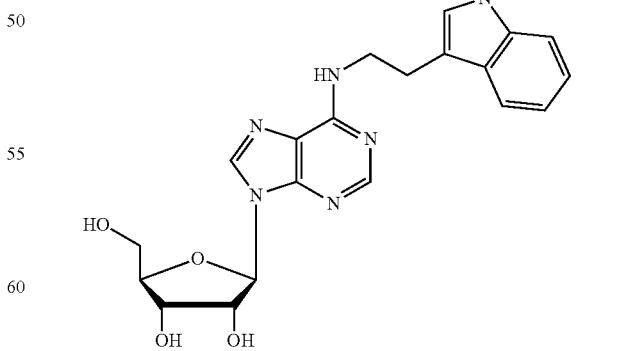

or a pharmaceutically acceptable salt thereof.

In further embodiments of the invention, the adenosine analog is a compound of formula (IV):

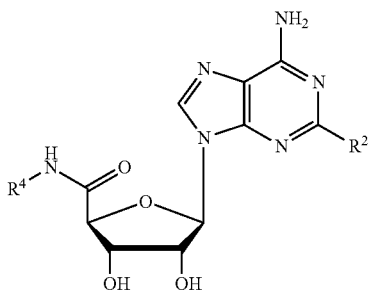

(IV)

or a pharmaceutically acceptable salt thereof.

In one preferred example of the compound of formula (IV) according to the invention, the adenosine analog is a compound having the formula CGS21680:

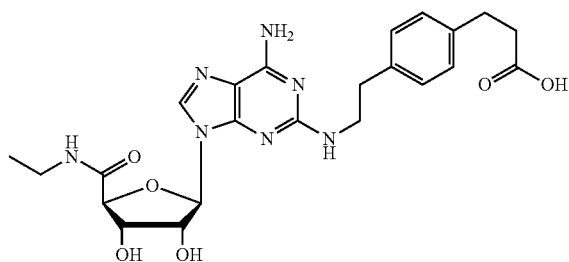

CGS21680 or a pharmaceutically acceptable salt thereof.

In some embodiments, the adenosine analog according to the present disclosure can be selected from the following:

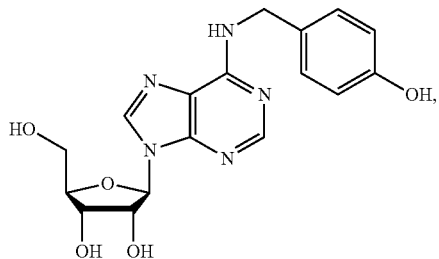

T1-11

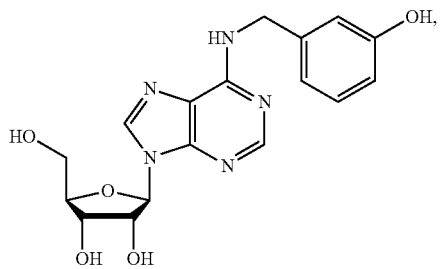

JMF1998

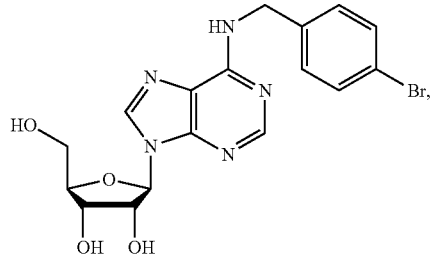

JMF2665

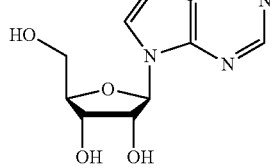

JMF1907 and

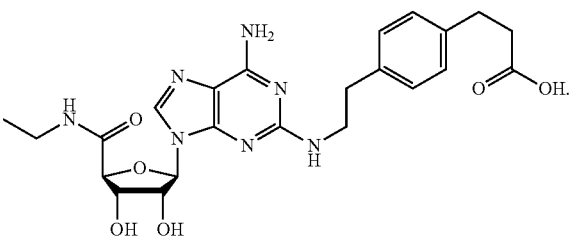

CGS21680

In another aspect, the present invention provides a pharmaceutical composition of use for treating pain (e.g., those described herein) comprising an effective amount of an adenosine analog as defined above, and a pharmaceutically acceptable carrier.

In further aspect, the present invention provides a method of treating pain, comprising administering to a subject in need thereof an effective amount of the adenosine analog as described herein, or a pharmaceutical composition comprising the adenosine analog as defined above.

Definitions

Unless otherwise defined, all technical and scientific terms used herein have the same meaning as commonly understood by one of ordinary skill in the art to which this invention pertains. In the case of conflict, the present document, including definitions will control.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, guinea pig, and the like).

As used herein, the terms "treatment," "treating," and the like, refer to obtaining a desired pharmacologic and/or physiologic effect. The effect may be prophylactic in terms of completely or partially preventing a disease or condition, or symptom thereof, and/or may be therapeutic in terms of a partial or complete cure for a condition and/or adverse affect attributable to the condition. The term "treatment" as used herein, covers any treatment of a disease or condition in a mammal, particularly in a human, and includes: (a) preventing the condition from occurring in a subject which may be predisposed to the condition but has not yet been diagnosed as having it; (b) inhibiting the development of the condition; and/or (c) relieving the condition, i.e., causing its regression.

As used herein, the phrase "an effective amount" refers to an amount sufficient to effect beneficial or desired results. An effective amount can be administered in one or more administrations. An effective amount corresponds with the quantity required to provide a desired average local concentration of a particular biologic agent, in accordance with its known efficacy, for the intended period of therapy. A dose may be determined by those skilled in the art by conducting preliminary animal studies and generating a dose response curve, as is known in the art. Maximum concentration in the dose response curve would be determined by the solubility of the compound in the solution and by toxicity to the animal model, as known in the art. The effective amount further corresponds with the quantity required to provide a desired average local concentration of the particular biologic agent, in accordance with its efficacy for the intended period of time. Due allowance can be made for losses due to circulatory fluctuation due to physical activity, for example, from ten to ninety percent loss allowance could be made depending upon the individual patient and their routines.

The term "pain" as used herein refers to an unpleasant feeling often caused by intense or damaging stimuli, including different types and symptoms of pain, either acute or chronic pain, especially inflammatory pain, cancer pain, chest pain, back pain, facial pain, joint pain, muscular pain syndromes, neuropathic pain, peripheral pain, cancer and tumor pain, sympathetic pain, postoperative pain, and post-traumatic pain.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference for the purposes or subject matter referenced herein.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The terms "alkenyl" and "alkynyl" are given their ordinary meaning in the art and refer to unsaturated aliphatic groups analogous in length and possible substitution to the alkyls described above, but that contain at least one double or triple bond respectively.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "aryl" or "Ar" as used herein is given its ordinary meaning in the art and refers to aromatic carbocyclic groups, substituted or unsubstituted, having a single ring (e.g., phenyl), or multiple fused rings, including phenyl, polyarene, and heterocycle comprising 5- or 6-membered ring or fused ring containing at least one nitrogen, oxygen or sulfur heteroatoms. Substituents include, but are not limited to the substituents recited for aliphatic moieties, or for other moieties as disclosed herein, resulting in the formation of a stable compound. In some cases, the heterocycle may be 3- to 10-membered ring structures or 3- to 7-membered rings, whose ring structures include one to four heteroatoms.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

All of the compounds described above may be in a variety of forms, including the compounds themselves, as well as their pharmaceutically acceptable salts, solvates, and hydrates, etc.

The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated by reference herein for the purposes or subject matter referenced herein. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

In certain embodiments, the compound is in the form of a hydrate or solvate. The term "hydrate" as used herein refers to a compound non-covalently associated with one or more molecules of water. Likewise, the term "solvate" refers to a compound non-covalently associated with one or more molecules of an organic solvent.

Uses of the prodrugs of the compounds described herein for treating pain is also within the scope of the present disclosure. Examples of prodrugs include esters and other pharmaceutically acceptable derivatives, which, upon administration to a subject, are capable of providing the indole compounds described above (see Goodman and Gilman's, The Pharmacological basis of Therapeutics, 8th ed., McGraw-Hill, Int. Ed. 1992, "Biotransformation of Drugs").

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

According to the present invention, it is unexpectedly found that adenosine analogs, which are effective for the treatment of pain through activation of neurokinin 1 (NK1) receptor signaling pathway in muscle nociceptors, thereby inducing the activation of activation of M-type potassium channel to induce outward currents. It is also found that the outward current is induced by M-type potassium channel in muscle afferent DRG neurons, and the activation of M-type potassium channel is mediated by NK1 receptor signaling in muscle afferent DRG neurons.

Accordingly, the invention provides a use in the manufacture of a medicament for treating pain of an adenosine analog that activates NK1 receptor signaling, thereby inducing outward current.

In the invention, mice lacking SP signaling were used to determine the contribution of SP to muscle pain sensitivity, and it is found that in contrast to the neurotransmitter's usual excitatory role, mice without SP signaling showed increased pain sensitivity after intramuscular acid injections as compared with mice that had normal SP signaling. Increased sensitivity to muscle pain was noted in mice lacking the gene for SP signaling as well as mice administered compounds designed to bind SP receptors.

Figure 5:
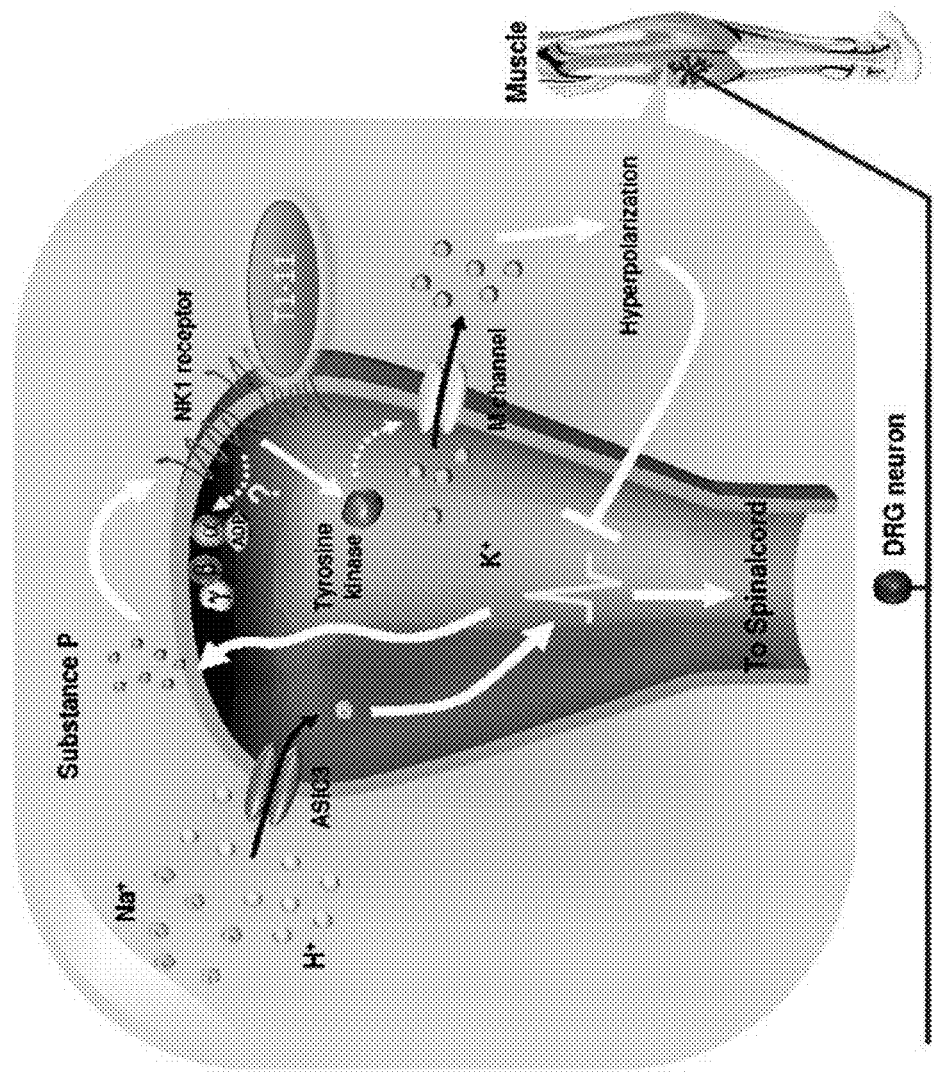
FIG. 5 provides a schematic model of antinociception in ASIC3-expressing muscle nociceptors, showing that the adenosine analogs according to the invention, such as the compound T1-11, target on a novel analgesic pathway.

It was also found in the invention that the antinociceptive effect of SP signaling involved the activation of NK1 receptor on muscle nociceptors. FIG. 5 illustrates a schematic model of the T1-11 antinociception in ASIC3-expressing muscle nociceptors. When tissue acidosis occurs in muscle, protons depolarize the muscle afferents, and T1-11 acts on the NK1 associated with receptor in the local nerve terminals. The NK1 receptors on muscle afferents are coupled with an unconventional signal pathway by activating M channels via a G-protein-independent, tyrosine kinase-dependent manner.

Accordingly, the invention provides a use in the manufacture of a medicament for treating pain of an adenosine analog that activates NK1 receptor signaling, thereby inducing outward current.

It is evidenced the adenosine analog according to the invention is effective for treating acid-induced pain in term of the effects of T1-11 in inhibition of acid-sensing ion channel 3 (ASIC3) in muscle nociceptors. That is, the pain may include the pain associated with tissue acidosis, and the pain is associated with muscular origin, such as in muscle afferent DRG neurons. Accordingly, it is expected that the pain to be treated includes acid-induced pain, such as acid-induced muscle pain, particularly an acid-induced chronic muscle pain.

According to the invention, the pain may include inflammatory pain, cancer pain, chest pain, back pain, facial pain, joint pain, muscular pain syndromes, neuropathic pain, peripheral pain, cancer and tumor pain, sympathetic pain, postoperative pain, and post-traumatic pain. In some embodiments, the pain is fibromyalgia, myofascial pain, bladder pain syndrome or pain caused by irritable bowel syndrome.

In the invention, it was evidenced in Examples that some adenosine analogs, such as an adenosine analog having the formula T1-11 ("the compound T1-11" or "T1-11"), was proven to be effective in treating pain, particularly acid-induced pain.

The compound T1-11 is known as 2-(6-(4-hydroxybenzylamino)-9H-purin-9-yl)-5-(hydroxymethyl)-tetrahydrofuran-3,4-diol, which may be isolated from *Gastrodia* extract, such as from the roots. (See also U.S. Pat. No. 7,351,434 at col. 20, lines 4-22.) The compound T1-11 was proven to activate neurokinin 1 (NK1) receptor signaling, and to be antinociceptive in ASIC3-mediated pain model. A low dose of T1-11 (4 pmole) still had analgesic effects on acid-induced chronic muscle pain models in mice (see FIG. 1). It was indicated that T1-11 mediated an outward current in SP-sensitive ASIC3-expressing muscle nociceptors and thus inhibited acid-induced ASIC3 activation (see FIG. 2(A)). The $EC_{50}$ of T1-11 for outward current is 1.3 nM as compared with SP of 2.6 µM (see FIGS. 2(B) & 2(C)). In addition to the compound T1-11, other adenosine analogs were also shown to mediate an outward current as potent as SP in muscle nociceptors (see Figure. 3).

According to the invention, the adenosine analog is a compound of Formula (I):

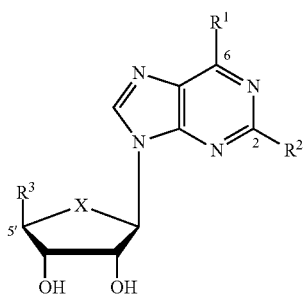

(I)

or a pharmaceutically acceptable salt, solvate, or hydrate thereof;

wherein:

X is O, S or $CH_2$, $R^1$ is selected from the group consisting of $NHR^4$, $NH(CH_2)_nR^4$, $NH-NHR^4$, $NHCONHR^4$, $NH-OR^4$, $O-NHR^4$, and $SR^4$;

$R^2$ is selected from the group consisting of hydrogen (H), halogen, cyano, $OR^4$, $NHR^4$, substituted or unsubstituted alkyl, substituted or unsubstituted alkenyl, substituted or unsubstituted alkynyl, substituted or unsubstituted cycloalkyl, substituted or unsubstituted aryl (Ar), substituted or unsubstituted aralkyl, and a substituted or unsubstituted heterocyclyl;

$R^3$ is selected from the group consisting of halomethyl, hydroxymethyl ($HOCH_2$), alkoxymethyl ($R^4OCH_2$), azidomethyl ($N_3CH_2$), aminomethyl ($H_2NCH_2$), substituted or unsubstituted aminomethyl, amidomethyl ($H_2NCOCH_2$), sulfanylmethyl ($R^4S$), sulfonylmethyl ($R^4SO_2$), triazolylmethyl, cyanomethyl ($N\equiv CCH_2$), cyano, substituted or unsubstituted carbonyl ($R^4CO$), COOH, substituted or unsubstituted aminocarbonyl ($R^4HNCO$), substituted or unsubstituted alkynyl, and substituted or unsubstituted tetrazole;

n is 1, 2 or 3;

each instance of $R^4$ is independently selected from the group consisting of H, alkyl, cycloalkyl, substituted or unsubstituted Ar, substituted or unsubstituted aralkyl, and a substituted or unsubstituted heterocyclyl;

Ar is selected from the group consisting of substituted or unsubstituted phenyl, substituted or unsubstituted polyarene, and a substituted or unsubstituted heterocycle.

In some embodiments, $R^2$ is hydrogen. In some embodiments, $R^2$ is halogen. In some embodiments, $R^2$ is cyano. In some embodiments, $R^2$ is $OR^4$. In some embodiments, $R^2$ is $NHR^4$. In some embodiments, $R^2$ is substituted or unsubstituted alkyl. In some embodiments, $R^2$ is substituted or unsubstituted alkenyl. In some embodiments, $R^2$ is substituted or unsubstituted alkynyl. In some embodiments, $R^2$ is substituted or unsubstituted cycloalkyl. In some embodiments, $R^2$ is substituted or unsubstituted aryl. In some embodiments, $R^2$ is substituted or unsubstituted aralkyl. In some embodiments, $R^2$ is a hydrocarbon chain wherein the carbon unit is substituted by one or more aryl groups. In some embodiments, $R^2$ is $C_{1-10}$ hydrocarbon chain with the carbon unit substituted by one or more aryl groups. In some embodiments, $R^2$ is substituted or unsubstituted heterocyclyl. In some embodiments, $R^2$ is 5- or 6-membered ring or fused ring containing at least one nitrogen, oxygen or sulfur heteroatoms.

In some embodiments, $R^4$ is substituted or unsubstituted aralkyl. In some embodiments, $R^4$ is a hydrocarbon chain with the carbon unit substituted by one or more aryl groups. In some embodiments, $R^4$ is a $C_{1-10}$ hydrocarbon chain with the carbon unit substituted by one or more aryl groups. In some embodiments, $R^4$ is substituted or unsubstituted heterocyclyl. In some embodiments, $R^4$ is 5- or 6-membered ring or fused ring containing at least one nitrogen, oxygen or sulfur heteroatoms.

In some embodiments, Ar is substituted or unsubstituted phenyl. In some embodiments, Ar is substituted or unsubstituted polyarene. In some embodiments, Ar is substituted or unsubstituted heterocycle. In some embodiments, Ar is substituted or unsubstituted heterocycle of 5- or 6-membered ring or fused ring containing at least one nitrogen, oxygen or sulfur heteroatoms.

In some embodiments of the invention, the adenosine analogs are respectively the compounds of Formula (II), Formula (III), and Formula (IV) as listed in Table 1 below, including but not limited to some examples, JMF1998, JMF2665, JMF1907 and CGS21680. The compounds described herein include salts, solvates, hydrates forms thereof.

TABLE 1

| Compound | Example |
|---|---|
| (II) | (T1-11) |

TABLE 1-continued

| Compound | Example |
|---|---|
| | JMF1998 |
| | JMF2665 |
| (III) | JMF1907 |
| (IV) | CGS21680 |

The compounds described herein can be prepared by conventional chemical transformations (including protecting group methodologies), e.g., those described in R. Larock, Comprehensive Organic Transformations, VCH Publishers (1989); T. W. Greene and P.G.M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

A compound thus synthesized can be further purified by flash column chromatography, high performance liquid chromatography, crystallization, or any other suitable methods.

Alternatively, the adenosine analog described herein (e.g., T1-11) can be isolated from its natural source (e.g., extracted from a *Gastrodia*). In one example, compound T1-11 can be isolated from a *Gastrodia* extract.

A listing of references related to the present invention, the contents of which are incorporated by reference for the purposes or subject matter referenced herein, includes: (1) U.S. Pat. No. 7,351,434, in part, disclosing the compound T1-11 and its chemical structure; (2) Huang et al., A new drug design targeting the adenosinergic system for Huntington's disease (PLoS ONE 2011; 6 (6) 220934, describing the isolation of T1-11 and the dual function of T1-11, and the potential application of T1-11 for treating Huntington's disease); (3) Lin et al., An antinociceptive role for substance P in acid-induced chronic muscle pain. *Proc Natl Acad Sci USA.*, 2012, describing that intramuscular substance P mediates an unconventional NK1 receptor signal pathway to inhibit acid activation in muscle nociceptors, which results in an unexpected anti-nociceptive effect against chronic mechanical hyperalgesia induced by repeated intramuscular acid injection; (4) Deval et al., Acid-sensing ion channels in postoperative pain. *J Neurosci* 31:6059-6066, 2011, describing that muscle nociceptors expressing ASIC3 was responsible for postoperative pain. Applying ASIC3 selective antagonist can effectively block the postoperative pain. Other publications cited herein are also incorporated by reference for the purposes or subject matter referenced herein.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Pharmaceutical Compositions

Pharmaceutical compositions of the present invention and for use in accordance with the present invention may include a pharmaceutically acceptable excipient or carrier. As used herein, the term "pharmaceutically acceptable carrier" or "pharmaceutically acceptable excipient" means a non-toxic, inert solid, semi-solid or liquid filler, diluent, encapsulating material or formulation auxiliary of any type. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum coreum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methyl pyrrolidone.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

In the invention, the pharmaceutical compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulations, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

The ointments, pastes, creams, and gels may contain excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain excipients such as lactose, talc, silicic acid, aluminum hydroxide, calcium silicates, and polyamide powder, or mixtures of these substances. Sprays can additionally contain customary propellants such as chlorofluorohydrocarbons.

It will also be appreciated that the compounds and pharmaceutical compositions of the invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for treating pain.

It will also be appreciated that certain of the compounds of the invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Accordingly, the invention also provides a pharmaceutical composition for treating pain, comprising:

(a) an adenosine analog as defined herein (e.g., formula I, II, III, or IV such as compound T1-11, JMF1907, JMF1998, JMF2665, and CGS21680), and (b) a further active agent for treating pain, wherein the further active agent is different from the adenosine analog.

Methods of Treatment

The present invention provides a method for treating pain comprising administering to a subject in need thereof a therapeutically effective amount of an adenosine analog, or a pharmaceutical composition as defined herein. The compounds according to the invention can enhance outward current induced by M-type potassium channel in muscle neurons. The activation of NK1 receptor signaling produces beneficial therapeutic effects on pain management.

In the invention, the pain to be treated may be associated with cardiovascular disease, stroke-induced neural damage, arthritis, cancer, inflammation, infection, oropharyngeal diseases or damage, traumatic injuries, acute and chronic cough, gastrointestinal disorders, central nervous system disorders, psychiatric diseases or manifestations.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex, and diet of the subject; the time of administration, mute of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, Tenth Edition, A. Gilman, J. Hardman and L. Limbird, eds., McGraw-Bill Press, 155-173, 2001, which is incorporated herein by reference in its entirety).

EXAMPLES

Materials and Methods

Animals.

Adult (8- to 12-wk-old) C57/BL6 mice were used. All procedures followed the Guide for the Use of Laboratory Animals (National Academy Press, Washington D.C., USA) and were approved by the Institutional Animal Care and Use Committee of Academia *Sinica*. We aimed to minimize the number of animals used and their suffering without compromising the quality of the experiments. The generation and genotyping of $Tac1^{-/-}$ mice and $Asic3^{-/-}$ mice were as described. Both null mutant mice were backcrossed to C57/BL6 for 10 generations to establish a congenic strain. Congenic $Tac1^{-/-}$ $Asic3^{-/-}$ mice were offspring of $Tac1^{+/-}$ and $Asic3^{+/-}$ intercrosses.

Mouse Model of Fibromyalgia.

To induce fibromyalgia-like symptoms, mice were treated with intermittent cold stress, which produces long-lasting (more than 2 weeks) thermal hyperalgesia and mechanical allodynia, predominantly in females. Method: Mice were placed on stainless mesh plate in a cold room at 4° C. overnight (from 4:30 pm to 10:00 am), followed by intermittent cold stress with environment temperatures alternating between 24 and 4° C. every 30 min, from 10:00 am to 4:30 pm. These procedures were repeated twice. On day 3, the mice were adapted to 24 C for 1 h before behavioral testing.

Behavioral Assays.

Mice received an intramuscular acid injection in the gastrocnemius muscle (GM) containing 20 μl acid saline (pH 4.0) with or without $(Sar^9, Met(O_2)^{11})$-substance P (SP; 4, 10, or 40 μM) or 100 μM RP67580 or 200 μM XE991. Mechanical hyperalgesia was assessed by applying a 0.2-mN von Frey filament to the plantar surface of both hind paws of mice. Mice were acclimatized in an acrylic cubicle for 60 min before testing. A positive response was defined as the foot lifting when the von Frey filament was applied. For each paw, the filament was applied 5 times at 30-sec intervals. Responses of the paw to mechanical stimuli were measured before injection and at 4 and 24 hr and 5 days after the first acid injection (day 0) and at 4, 24, and 72 hr and 1 week after the second acid injection (day 5). For single-injection experiments, responses to mechanical stimuli were measured before the injection, at 4 hr and at 1, 3, 5, 7, 9, 11, 13, 15 and 22 days after the injection or at 4, 24, 48 hr and 7 and 14 days after the injection. NK1-selective agonist $((Sar^9, Met(O_2)^{11})$—SP) was from Sigma Chemical (St. Louis, Mo.). NK1-selective antagonist (RP67580) and XE991 were from Tocris (Avonmouth, UK). The experimenters were blinded to the experimental manipulations. The person who conducted von Frey test had no information of the mouse genotypes or drug injections.

Plasma Extravasation.

Mice were intraperitoneally injected with 1% Evans Blue dye (EB, E2129-10G Sigma) (W/V in phosphate buffered saline), which was sterilized by passage through Millex-GS 0.22-μm filter (Millipore). Then 24 hr later, mice were injected with 20 μl solution (pH 7.4 saline, pH 4.0 saline, 40 μM SM-SP, or 20% mustard oil) into the left GM. At 30 min after intramuscular injection, the right and left GM were individually dissected, weighed, diced, and placed in 4 ml of 99% formamide at room temperature (21-25° C.) for 72 hr. The samples were centrifuged at 2,000 rpm for 20 min. The absorbance of the supernatant was determined spectrophotometrically at 620-nm wavelength. The dye content of samples was calculated from a standard curve of Evans Blue concentrations. Comparison between groups involved Mann-Whitney test. Drugs were purchased from Sigma Chemical.

Dorsal Root Ganglion (DRG) Primary Culture.

To retrograde-trace muscle-afferent DRG neurons, mice were injected with 4% Fluorogold (Fluorochrome, Denver, Colo.) into the GM of both legs for 5 to 7 days, then lumbar DRG neurons were dissected and removed from both sides and placed in a tube for digestion with 1 ml DMEM containing 0.125% type 1 collagenase for 90 min and 0.25% trypsin for 20 min at 37° C. The digested DRG neurons washed with fetal calf serum (FCS)-free DMEM or DMEM containing 10% FCS during each treatment. Fully digested DRGs were triturated and plated on poly-L-lysine-coated cover slides. Cell cultures were maintained in a 5% CO2 incubator at 37° C.

Whole-Cell Patch-Clamp Recording.

Whole-cell patch-clamp recordings of muscle-afferent neurons involved use of Axopatch MultiClamp 700B (Axon Instruments). Neurons with membrane potential >−40 mV were discarded. The bridge was balanced in current-clamp recording, and the series resistance was compensated 70% in voltage-clamp recording with Axopatch 700B compensation circuitry. All experiments were performed at room temperature (21-25° C.) and completed within 30 hr post-seeding. Unless specifically mentioned, the patch pipettes were prepared in 1-5 MΩ and filled with internal solution containing (in mM) 100 KCl, 2 $Na_e$-ATP, 0.3 $Na_3$-GTP, 10 EGTA, 5 $MgCl_2$, and 40 HEPES, adjusted to pH 7.4 with KOH. Recording cells were superfused in artificial cerebrospinal fluid (ACSF) by control with gravitational force. The ACSF contained (in mM) 130 NaCl, 5 KCl, 1 $MgCl_2$, 2 $CaCl_2$, 10 glucose, and 20 HEPES, adjusted to pH 7.4 with NaOH. Osmolarity was adjusted to 300 mOsm. The acidic ACSF was titrated to pH 6.8 by 1 M NaOH. SP was prepared from a 300-μM stock solution to a final concentration of 3 μM in ACSF. In the experiment confirming potassium channel as the ion channel responsible for generation of outward current, NaCl was replaced with Tetraethyl ammonium chloride and pH was adjusted with CsOH. If not specifically mentioned, drugs listed above were from Sigma Chemical (St. Louis, Mo.). Reagents used in the study of SP-induced outward current were from Sigma (GDP-β-S) or Tocris Bioscience (RP67580, GR159897, SB218795, genistein, PP1, sodium orthovanadate, daidzein, XE991 and Linopirdine dihydrochloride).

Effect of SP on Acid-Induced Electrophysiological Responses.

Voltage-clamp mode was used to examine the effect of SP on acid-induced currents in ASIC3-expressing DRG neurons. A total of 40 GM and 6 non-GM DRG neurons were recorded in voltage-clamp mode with Vm held at −70 mV. In this study, we focused on the salicylic acid (SA)-sensitive (SAS) neurons with acid-induced current inhibited by SA because they represent ASIC3-expressing neurons. DRG neurons were treated with pH 6.8 acidic ACSF for 4 sec in each 30-sec time frame; 500 μM of SA in the bath was used for cell-type selection. Next, SA-containing bath was replaced with normal ACSF for 2 min, then a bath containing 3 μM SP for 3 min to record acid-induced current in the presence of SP. Finally, the SP-containing bath was replaced with normal bath for another 3 min. The nonhydrolysable form of GDP (GDP-β-S, 1 mM, from Sigma) was loaded in recording pipettes and dialysed for 10 min before recording. The effect of GDP-β-S was examined in an SP-containing bath and stimulated with acid for 3 min. In the end, the bath was switched back to normal ACSF and stimulated for another 3 min. To validate whether the modulation of SP on acid-induced current was NK1-receptor specific, acid-induced current was first recorded in a bath containing 10 μM RP67580 for 2 min as a control response. Next, the recording was performed in the bath containing both RP67580 and SP for 2 min, then one containing RP67580 alone. Phosphotyrosine kinase was tested for its role in SP-directed modulation on acid-induced current. Acid-induced current was recorded in a bath containing both SP and genistein (30 μM; Tocris), or both SP and daidzein (30 μM; Tocris) for 3 min. In addition, recording was performed in SP- and genistein-only bath as positive and negative controls, respectively.

SP-Induced Currents.

Voltage-clamp mode was used to detect SP-induced currents, and neurons were held at −70 mV. SP in ACSF solutions (3 μM) was puffed through a valve controller-controlled glass pipette towards the recording neurons for 4 sec with a 30-sec interval. The procedure was repeated at least 2 times to ensure consistent data. The SP-induced current tested under different pharmacological compounds was performed in triplicate. ACSF-containing compounds were superfused for 1 min to ensure complete replacement of previous perfusate between treatments. Then, the test compounds were washed away with ACSF, and SP-induced currents after the washout were examined 3 times. A neuron was defined as SP sensitive when the induced current was >10 pA (or <−10 pA with an outward current). To further verify the independency of $I_{SP-O}$ on GTP, Baclofen-induced GABA-B current served as a positive control. A recording pipette containing 1 mM GDP-β-S was used in GTP dialysis. The GABA-B current was induced by 100 μM Baclofen at the beginning of dialysis (0, 1 and 2 min after whole-cell patch clamp). Then, Baclofen was used to re-stimulate the dialyzed neurons after 10-min dialysis (10, 11 and 12 min after whole-cell patch clamp). Then, SP was used to verify the presence of $I_{SP-O}$ in the absence of GTP.

Voltage-Gated Sodium Currents.

To study the involvement of NK1 receptor and the M channel in modulating neuronal excitability under the influence of protons, mice were first injected with retrograde tracer 2 days before the injection of acidic saline (pH 4.0, 20 μl) or in combination with 100 μM RP67580 or 200 μM XE991. The treated mice were then killed and used for DRG culture 2 days later. For mice that received 2 injections of pH 4.0 saline, the second injection was given 2 days after the first injection and the mice were also killed 2 days after the second injection. DRG culture was as stated above and used for studying the voltage-gated sodium currents. The internal solution contained (in mM) 10 NaCl, 110 CsCl, 20 tetraethylammonium-Cl, 2.5 $MgCl_2$, 5 EGTA, 3 $Mg_2^+$-ATP, and 5 HEPES, adjusted to pH 7.0 with CsOH. The external solution for voltage-gated sodium current contained (in mM) 100 NaCl, 5 CsCl, 30 tetraethylammonium-Cl, 1.8 $CaCl_2$, 1 $MgCl_2$, 0.1 $CdCl_2$, 25 glucose, 5 4-aminopyridine, and 5 HEPES, adjusted to pH 7.4 with HCl. Osmolarity was adjusted to approximately 300 mOsm with glucose. DRG neurons with cell diameter between 30~40 μm were selected for recording. The voltage-gated sodium currents were evoked by a 30-msec test pulse at −40 mV from a holding potential of −80 mV. Recordings were performed in external solution with or without 200 nM tetrodotoxin (TTX; Tocris Bioscience, Avonmouth, UK).

Action Potential Threshold.

The action potentials of GM DRG neurons of different experimental groups were evoked by various voltages, and the threshold was defined as the beginning of the steep upward rise of the action potential.

Data Analysis.

Figure 2:
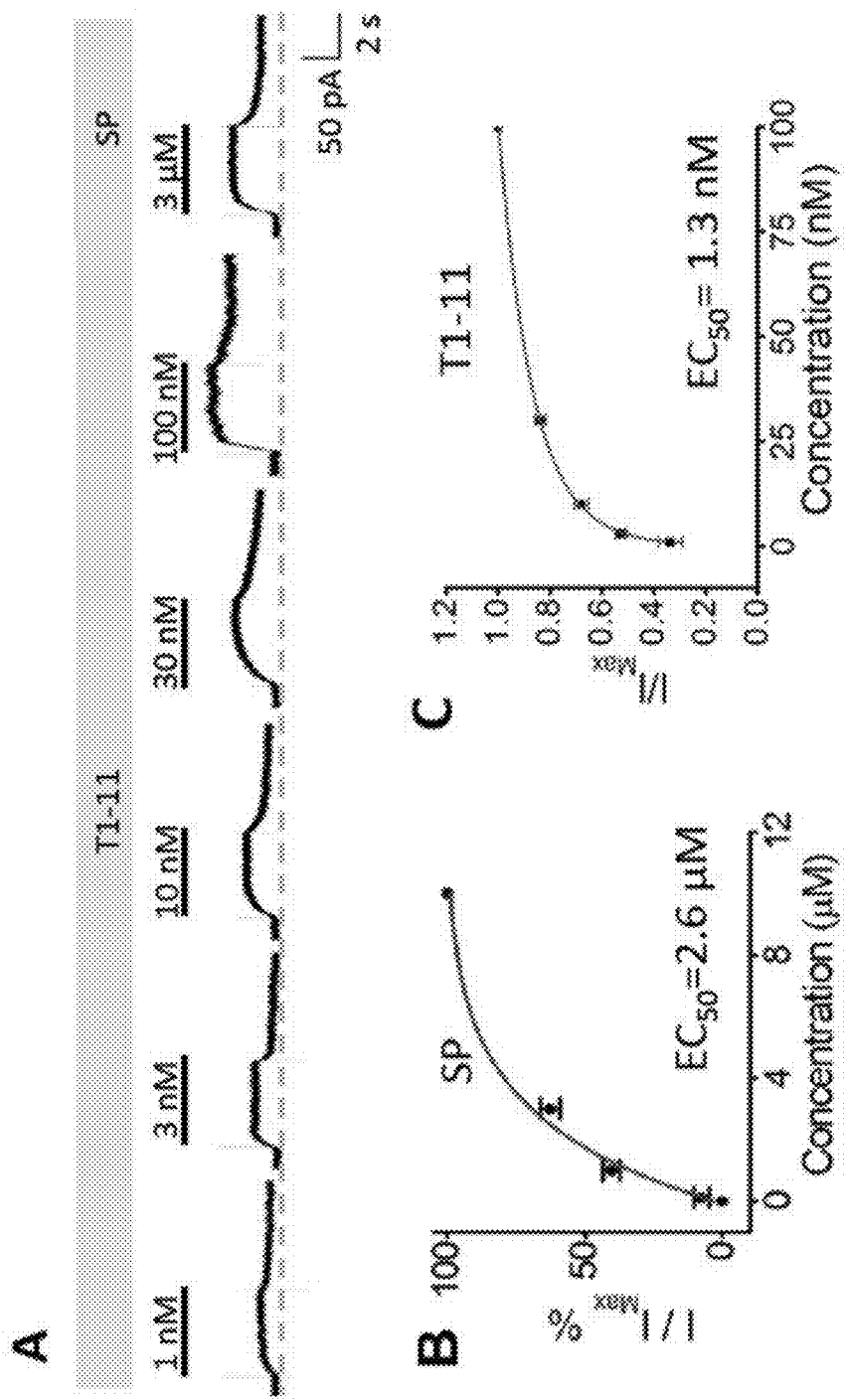
FIG. 2 shows that the compound T1-11 induced an outward current in muscle nociceptors. Panel A: a diagram showing that the compound T1-11 elicited a slow inactivating outward current ($I_{T1-11}$) in a dose-dependent manner in muscle nociceptor expressing SP-induced outward ($I_{SP-O}$). Panel B: a chart showing the peak whole-cell current amplitude as a function of $I_{SP-O}$, and dose-dependent (0.1, 1, 3, and 10 µM) of $I_{SP-O}$ with an $EC_{50}$ of 2.6 µM is shown (n=27). Panel C: a panel showing the peak whole-cell current as a function of $I_{T1-11}$, and dose-dependent (1, 3, 10, 30, and 100 nM) of $I_{T1-11}$ with an $EC_{50}$ of 1.3 nM is shown (n=11).

Results are presented as mean±SEM and analyzed by use of Origin 8.0 (OriginLab, Northampton, Mass.). One-way ANOVA then Fisher LSD post-hoc test was used to calculate differences between groups (FIG. 2). Other electrophysiological data were analyzed by paired or unpaired Student's t test as appropriate. The Mann-Whitney U test was used to compare withdrawal responses to von Frey filament in mice between before acid injection (baseline) and each time point after intramuscular acid-injection. A $P<0.05$ was considered statistically significant.

Results

T1-11 Analgesia

Figure 1:
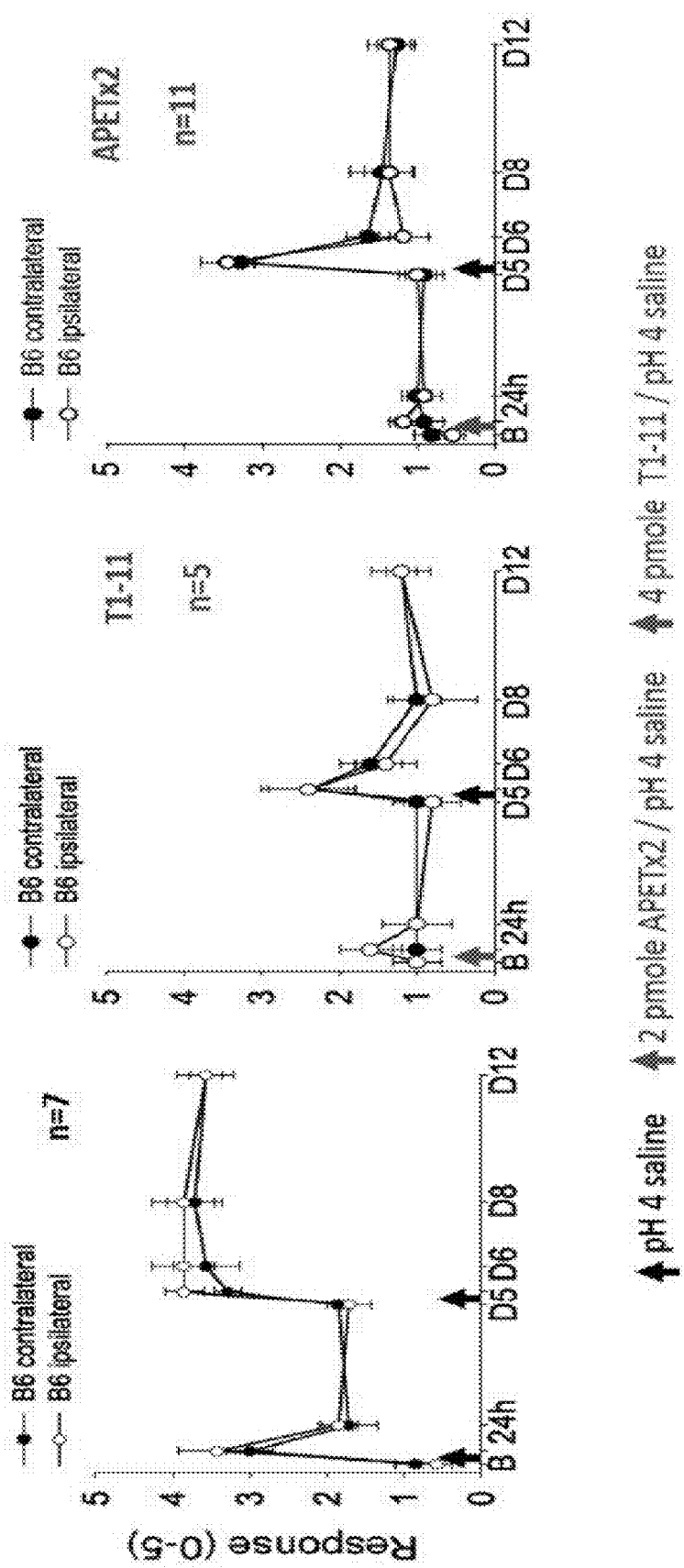
FIG. 1 shows the effects of the compound T1-11 in inhibition of acid(ASIC3)-induced chronic muscle pain in mice; wherein the ASIC3-dependent chronic muscle pain was induced by repeated injections of acid saline (pH 4.0, 20 µl) to one side of gastrocnemius muscle. As found in FIG. 1, the first acid-injection induced a transient hyperalgesia in mouse hind paws that attenuated at 24 h, whereas the second acid injection (in 5 days) caused a bilateral long-lasting mechanical hyperalgesia for more than 2 weeks (left panel). The co-injection of acid and T1-11 (middle panel) or APETx2 (a selective ASIC3 antagonist, right panel) abolished the transient hyperalgesia and prevented the development of chronic hyperalgesia induced by repeated acid injection.

It was found that the compound T1-11 had analgesic effect on acid-induced chronic muscle pain, in which the muscle pain was induced by repeated injection of acid saline (pH 4.0, 20 μl) to one side of gastrocnemius muscle (GM). The first acid injection induced rapid, transient referred hyperalgesia, which declined after 24 h; a second acid injection administered 5 day after the first induced long-lasting (>2 weeks) referred hyperalgesia. The acid-induced muscle pain is ASIC3-dependent. Co-injection of acid with ASIC3 antagonist APETx2 (2 pmole) at the first injection abolished the development of chronic hyperalgesia induced by the second acid injection. T1-11 (4 pmole) has the similar potency with APETx2 in inhibition of the acid-induced chronic hyperalgesia (FIG. 1).

The cellular basis of the T1-11 analgesia is that T1-11 induces an outward current ($I_{T1-11}$) in ASIC3-positive muscle afferent DRG neurons that also express substance P (SP)-induced outward current ($I_{SP-O}$). The $EC_{50}$ of is 1.3 nM as compared with $I_{SP-O}$ 2.6 μM (FIG. 2).

Figure 3:
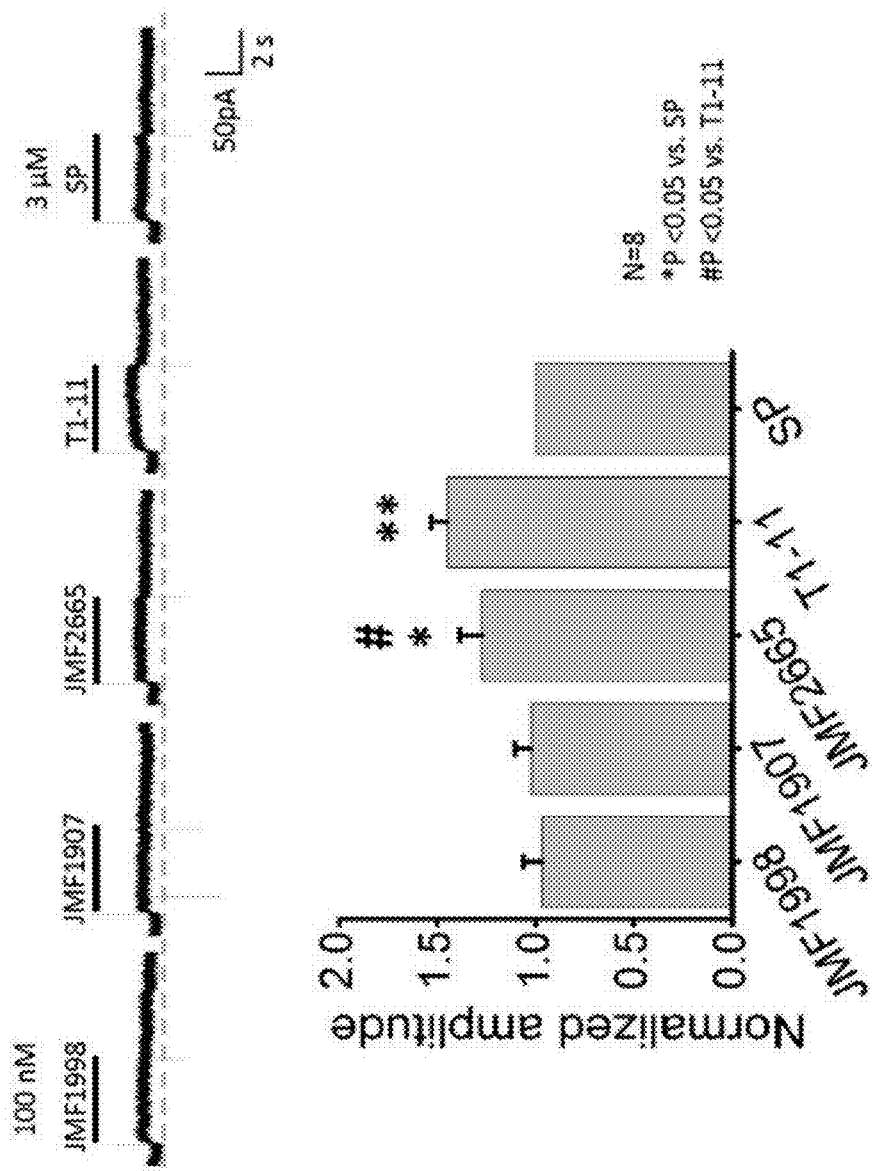
FIG. 3 shows the effect of some adenosine analogs including T1-11 and JMF1998, 1907 and 2665 on SP-sensitive muscle nociceptors, wherein the upper panel shows the representative traces for adenosine analogs, JMF1998, 1907 and 2665, mediated outward currents in a muscle nociceptor; and the lower panel shows the relative potency of T1-11, JMF1998, 1907 and 2665, to induce an outward current in muscle nociceptors as compared with SP (n=8).
Figure 4:
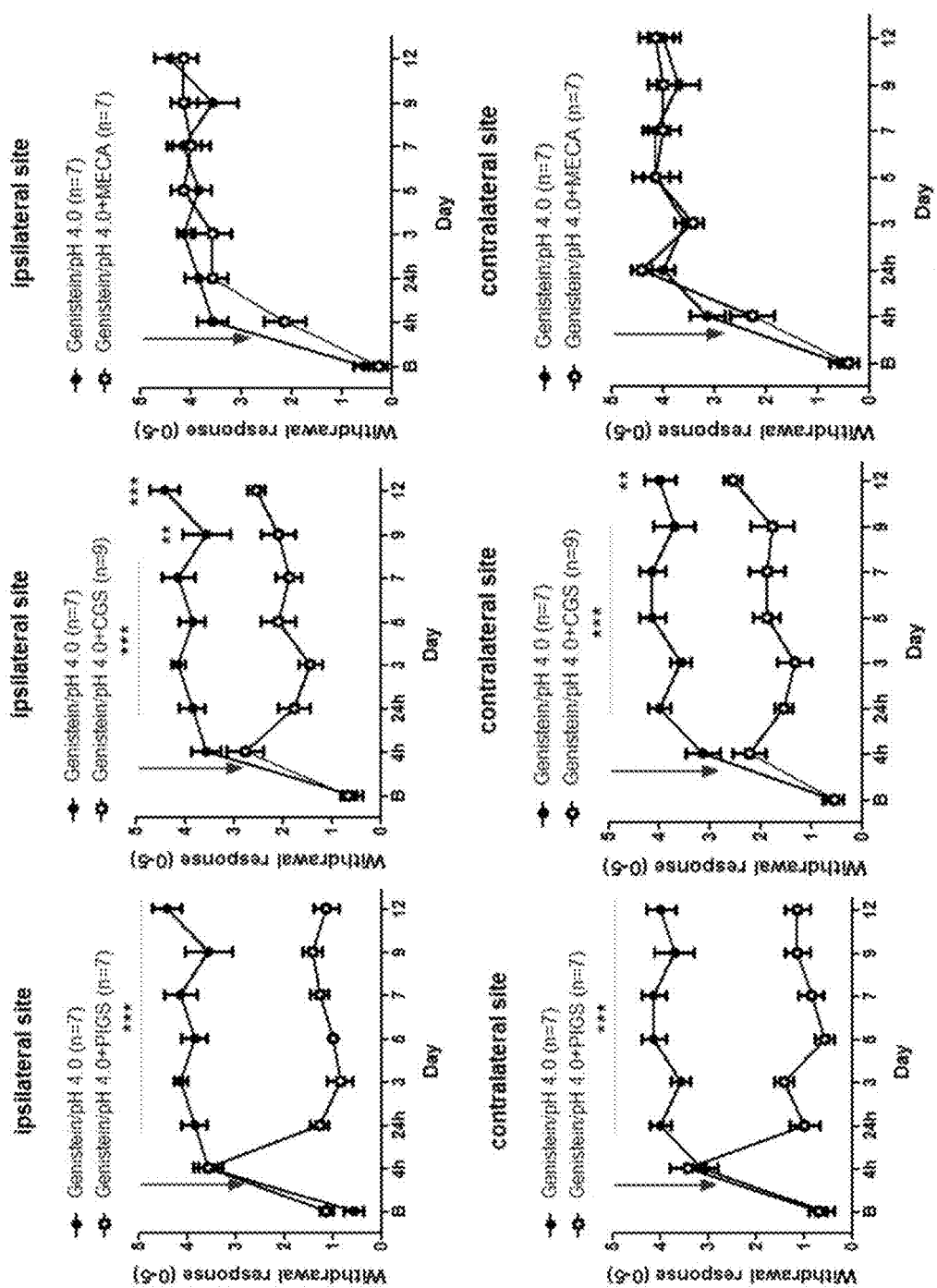
FIG. 4 shows the effects of the compound CGS21680 on acid-induced muscle pain; wherein a co-injection of the compound CGS21680 (1 nmole, i.m.) and acidic saline partially inhibited acid-induced hyperalgesia, and a co-injection of an A3 agonist, IB-MECA (1 nmole, i.m.) as a control has no effect on acid-induced hyperalgesia.

T1-11 analogues, such as JMF1998, 1907, 2665, CGS21680, can also induce outward currents in the ASIC3/SP-expressing muscle DRG neurons (see FIGS. 3 and 4). Co-injection of A2AR agonist CGS21680 (I nmole, i.m.) and acidic saline partially inhibited acid-induced hyperalgesia, whereas co-injection of A3 agonist IB-MECA (1 nmole, i.m.) has no effect on acid-induced hyperalgesia.

A new schematic model of T1-11 antinociception in muscle nociceptors was concluded and illustrated in FIG. 5. When tissue acidosis occurs in muscle, protons depolarize the muscle afferents. T1-11 acts on the NK1-associated receptor in the local nerve terminals. The NK1-associated receptors on muscle afferents are coupled with an unconventional signal pathway by activating M channels via a G-protein-independent, tyrosine kinase-dependent manner.

Figure 6:
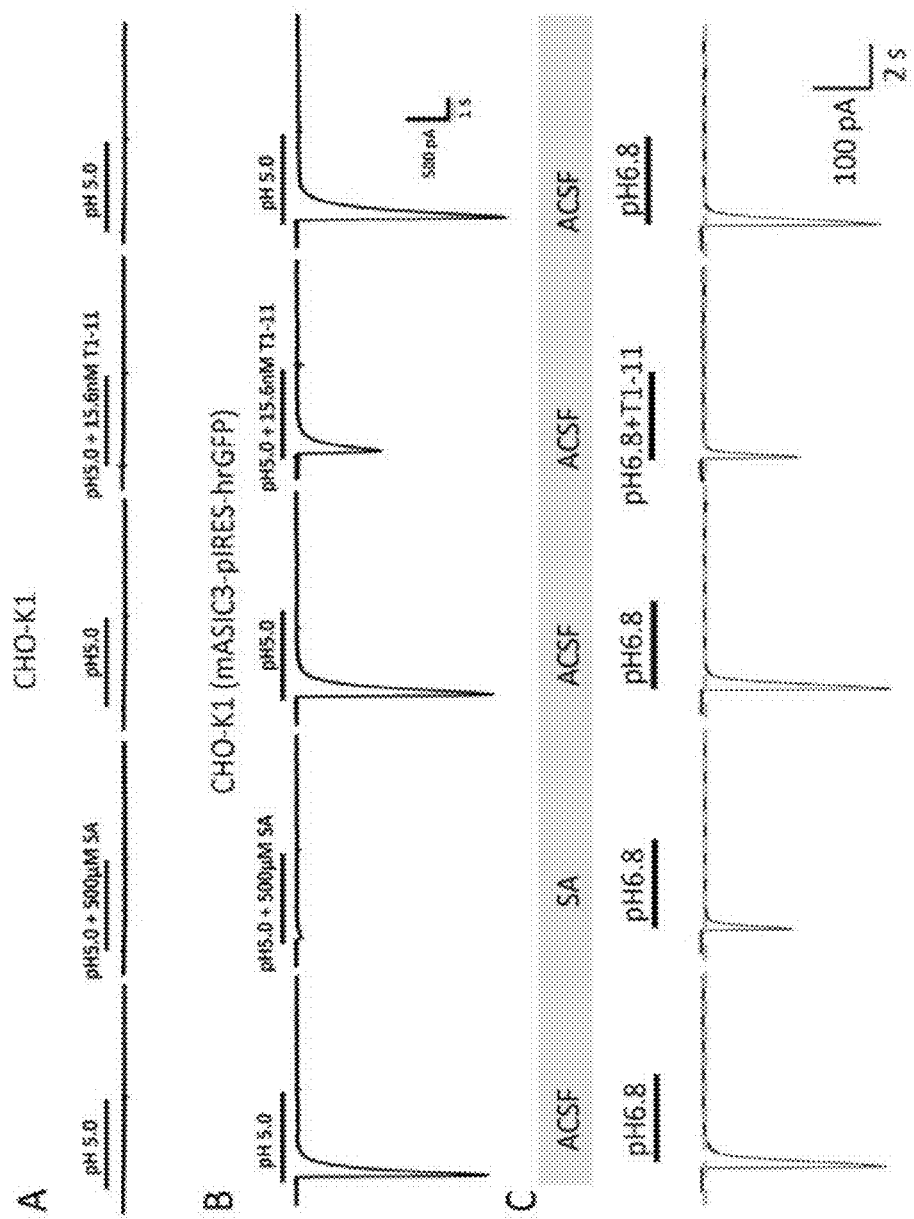
FIG. 6 shows that whole-cell patch clamp recordings revealed the inhibition of ASIC3-mediated current by the compound T1-11. Pane A: a diagram showing that no acid-induced current was found in CHO cells without ASIC3 transfection. Panel B: a diagram showing that the acid-induced current was blocked by salicylic acid (SA, a selective antagonist for ASIC3), and T1-11 in CHO cells transfected with ASIC3. Panel C: a diagram showing that the compound T1-11 (10 nM) inhibited acid-induced current in all ASIC3-expressing muscle nociceptors (n=9).

Whole-cell patch clamp recordings revealed the inhibition of ASIC3-mediated current by T1-11. In CHO cells transfected with ASIC3, the acid-induced current was blocked by salicylic acid (SA, a selective antagonist for ASIC3), and T1-11. (C) In all ASIC3-expressing muscle nociceptors, T1-11 in low dose (10 nM) is enough to inhibit acid-induced current (see FIG. 6).

Figure 7:
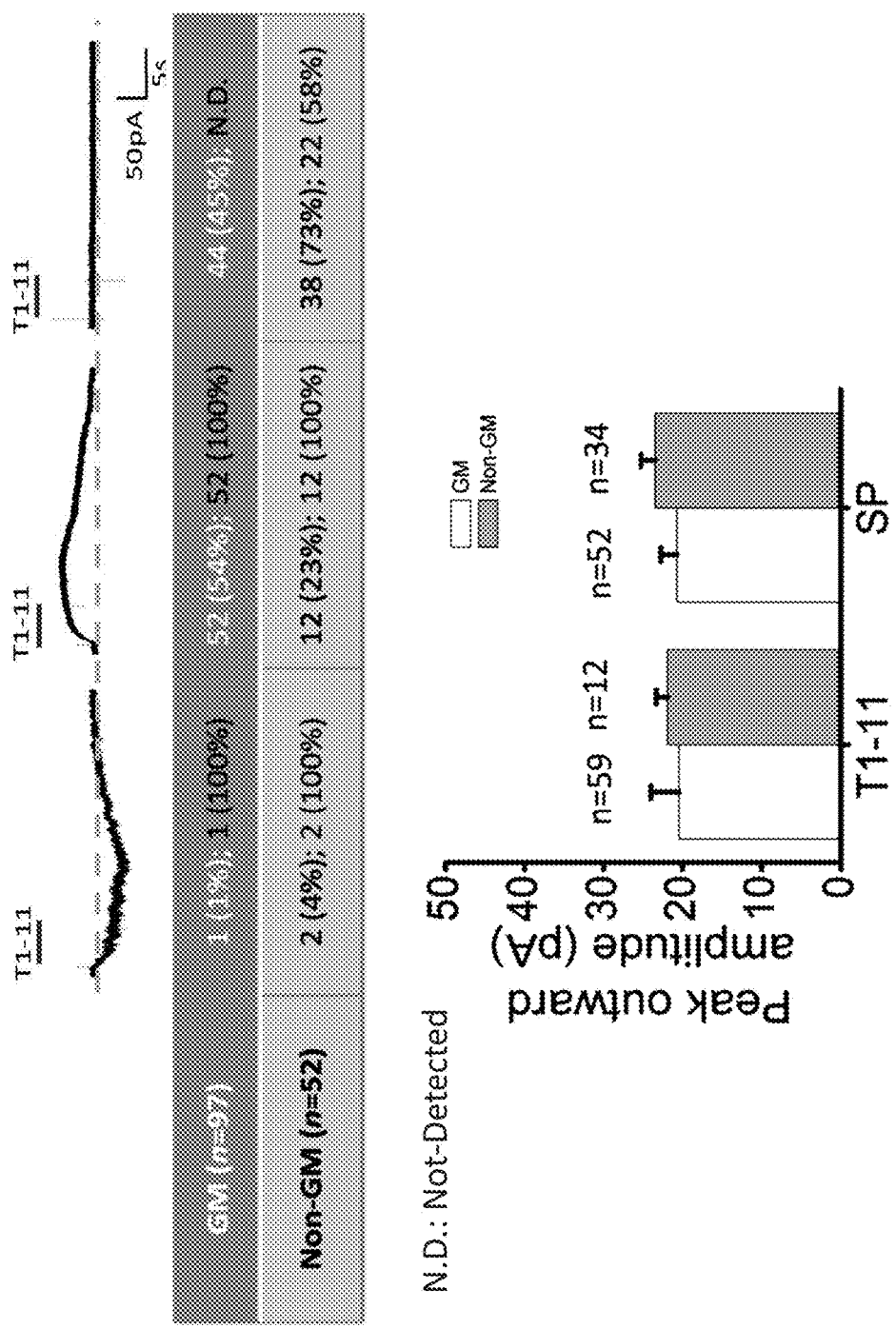
FIG. 7 shows that the compound T1-11 mediated currents in muscle DRG neurons; wherein the upper panel shows the T1-11-induced electrophysiological responses resulting from superfusion of 100 nM T1-11 for 4 s in GM-afferent DRG neurons and non-GM-afferent DRG neurons (including the number of neurons and percentage for each type of responses); and the lower panel shows the mean peak outward current of T1-11 (100 nM), that is similar to that of 3 µM substance P.

As shown in FIG. 7, the upper panel shows T1-11-mediated currents found in muscle DRG neurons (see the upper panel), and T1-11-induced electrophysiological responses resulting from superfusion of 100 nM T1-11 for 4 s in GM-afferent DRG neurons and non-GM-afferent DRG neurons, including the number of neurons and percentage for each type of responses. The lower panel shows the mean peak outward current of T1-11 (100 nM) is similar to that of 3 μM substance P.

T1-11 Pharmacology

The $I_{T1-11}$ is predominantly expressed in muscle afferent DRG neurons but not other sensory neurons. We then determined the molecular basis of in muscle nociceptors. $I_{T1-11}$ is reversely inhibited by A3 adenosine receptor antagonists (MRS1220, MRE3008F20) but not by A2A adenosine receptor antagonist (ZM241385), indicating the involvement of A3 adenosine receptors. Although T1-11 was known bound to A2A adenosine receptors in neurons of central nervous system, we showed that is not changed in A2A$^{-/-}$ muscle afferent DRG neurons. We also found that A3 adenosine receptor antagonist (MRS1220, 200 pmole i.m.) abolished the analgesic effect of T1-11 on acid-induced muscle pain model, which further demonstrates the involvement of A3 adenosine receptors in $I_{T1-11}$. However, A3 adenosine receptor agonist (IB-MECA, 1 nmole i.m.) did not have analgesic effect on acid-induced muscle pain. Instead, A2A adenosine receptor agonist (CGS21680, 1 nmole i.m.) showed partial analgesic effect on the acid-induced muscle pain (FIG. 4). Accordingly, CGS21680 in high dose (10 μM) induces an outward current in A2A$^{-/-}$ muscle afferent DRG neurons, indicating CGS21680 is a partial agonist for the $I_{T1-11}$.

The involvement of NK1 receptor in was further determined because NK1 receptor antagonist RP67580 (10 n=17) inhibited $I_{T1-11}$. Like $I_{SP-O}$, $I_{T1-11}$ is resistant to GTP dialysis and mediated via M-type potassium channel. T1-11 enhanced M current in voltage shift from −50 mV to −20 mV in muscle afferent neurons expressing $I_{SP-O}$. These results indicated that T1-11 enhanced M-type potassium currents through the NK1-associated receptors in a G-protein-independent manner. A3 adenosine receptors were proven to be involved in the NK1-associated receptor complex.

Therapeutic Effect of $T_{1-11}$ on Fibromyalgia

Figure 8:
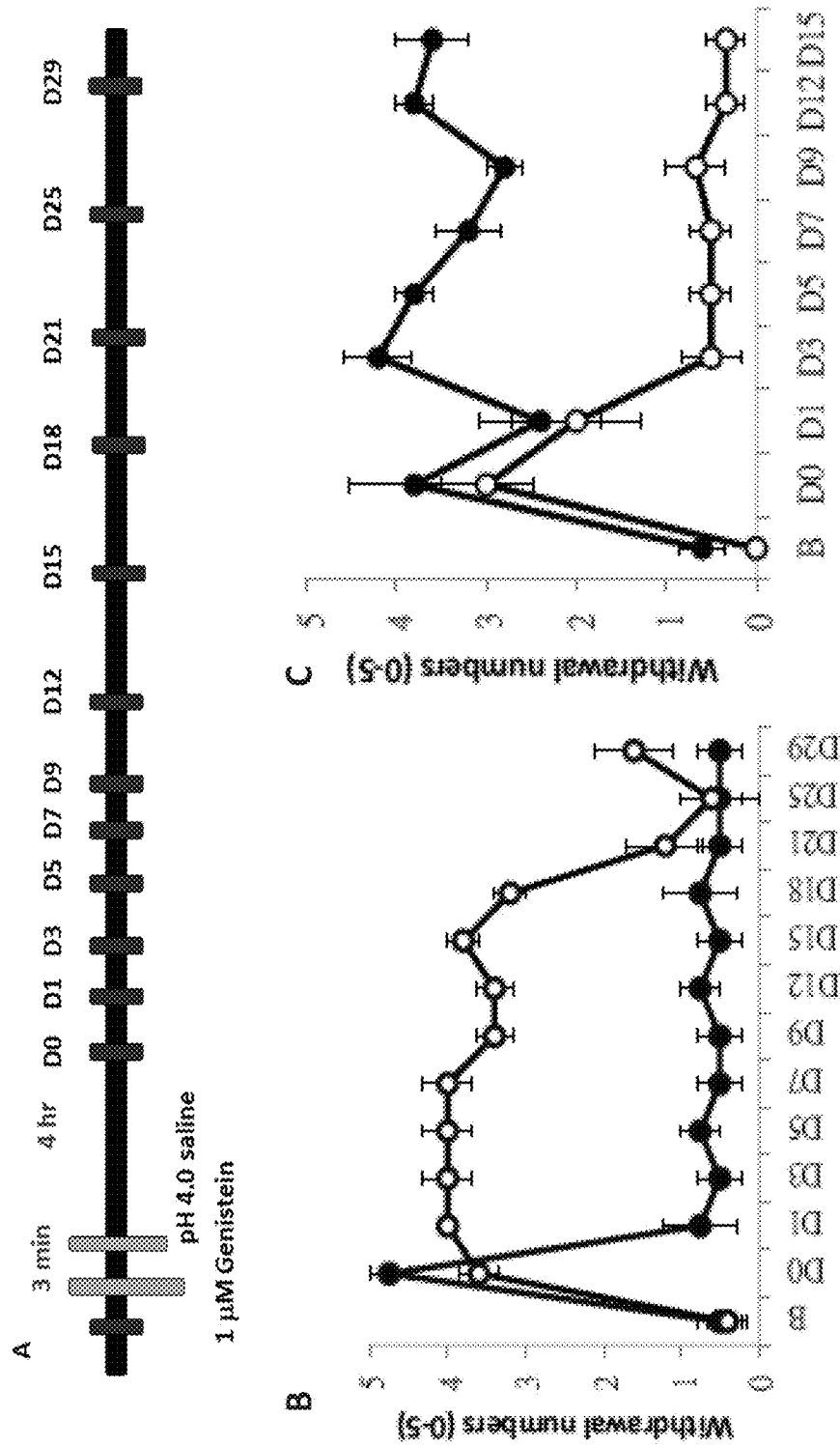
FIG. 8 shows that the compound T1-11 had the analgesic effect on a modified acid-induced chronic muscle pain model. Panel A: a diagram showing that mice were first received an intramuscular injection of genistein (a tyrosine kinase inhibitor) and an acid saline to one side of gastrocnemius muscle, and then pain behaviors were assayed by using von-Frey filament test at 4 hr (D0) and until 29 days (D29) after acid injection. Panel B: is a chart showing that the single acid injection induced long-lasting chronic hyperalgesia in mice with genistein pretreatment (open circles, n=5), but only transient hyperalgesia in mice without genistein pretreatment (filled circles, n=4). Panel C: a chart showing the effect of genistein pretreatment that can be reversed by co-injection of acid and the compound T1-11 (open circle, n=6), which only showed the transient hyperalgesia, but not the vehicle (filled circles, n=5).

It was further shown that T1-11 was an excellent therapeutic compound in two mouse models of fibromyalgia. The first model was the acid-induced chronic muscle pain model, in which mice developed chronic muscle after intramuscular acid injection and a genistein treatment (see FIG. 8). T1-11 showed a dose-dependent analgesic effect on mice that have developed the chronic muscle pain wherein the doses of T1-11 were in the range of 75-150 μg/kg (i.p.).

Figure 9:
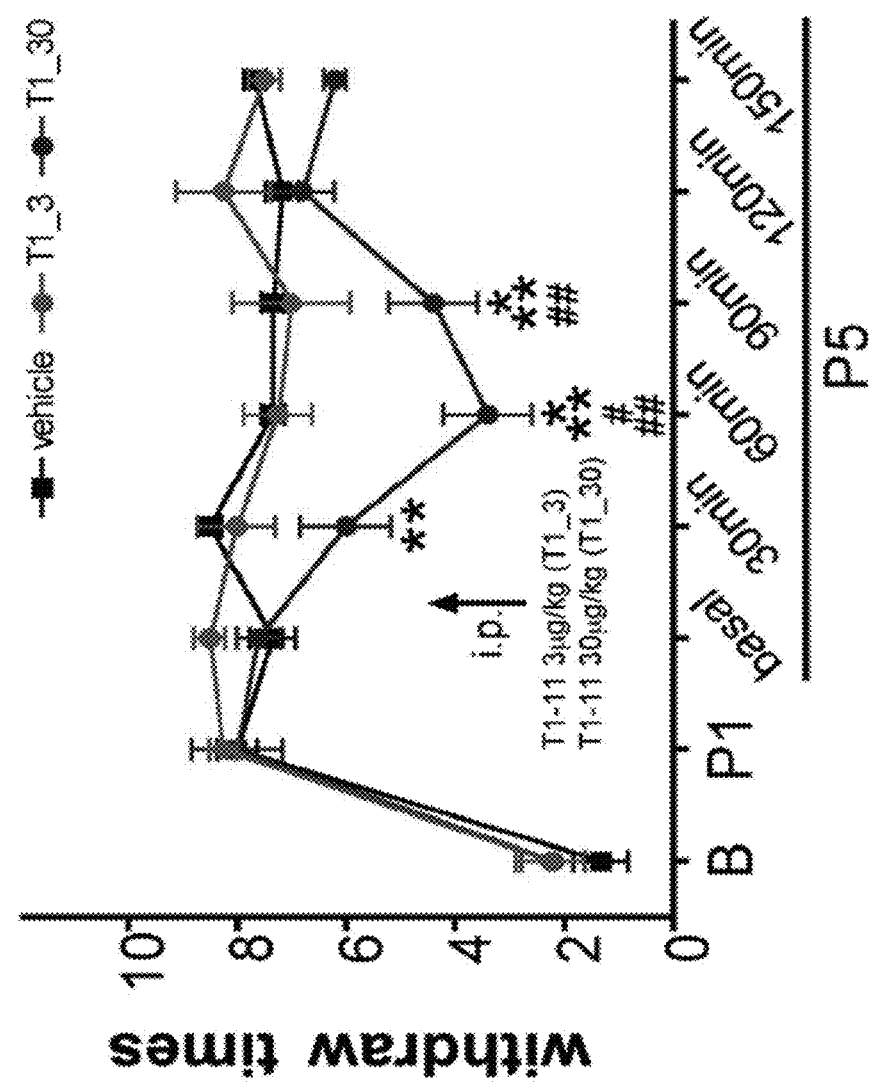
FIG. 9 shows the analgesic effect of the compound T1-11 on a mouse model of fibromyalgia; wherein T1-11 (30 ug/kg) had analgesic effect on mice treated with ICS. Mechanical hyperalgesia was assessed by applying a 0.2 mN von Frey filament to the plantar surface of both hind paws. For each paw, the filament was applied for 5 times at 30-s intervals.

The second fibromyalgia model is developed by Ueda's group, in which mice were treated with intermittent cold stress for 2 days (Nishiyori & Ueda, 2008). Mice treated with intermittent cold stress will develop long-lasting (>2 weeks) mechanical and thermal hyperalgesia. Analgesic effect of T1-11 was tested in these mice 5 day after intermittent cold stress (ICS). We found that T1-11 in 30 μg/kg (i.p.) was the therapeutic dose to treat the pain (see FIG. 9). Moreover, we found T1-11 and substance P have synergistic effect in treating the ICS-induced pain. T1-11 in 3 μg/kg or SM-substance P in 0.6 mg/kg (a selective agonist for NK1 receptor) alone did not show analgesic effect on the ICS-treated mice. However, combined T1-11 in 3 μg/kg with 0.6 mg/kg SM-substance P showed analgesic effect on the ICS-treated mice.

REFERENCES

1. Hokfelt T, Pernow B, & Wahren J (2001) Substance P: a pioneer amongst neuropeptides. *J Intern Med* 249(1):27-40.
2. Hokfelt T, Kellerth J O, Nilsson G, & Pernow B (1975) Substance p: localization in the central nervous system and in some primary sensory neurons. *Science* 190(4217):889-890.
3. Ji R R, Kohno T, Moore K A, & Woolf C J (2003) Central sensitization and LTP: do pain and memory share similar mechanisms? *Trends Neurosci* 26(12):696-705.
4. Basbaum A I, Bautista D M, Scherrer G, & Julius D (2009) Cellular and molecular mechanisms of pain. *Cell* 139(2):267-284.
5. Ikeda H, Heinke B, Ruscheweyh R, & Sandkuhler J (2003) Synaptic plasticity in spinal lamina I projection neurons that mediate hyperalgesia. *Science* 299(5610):1237-1240.
6. McMahon S B, Sykova E, Wall P D, Woolf C J, & Gibson S J (1984) Neurogenic extravasation and substance P levels are low in muscle as compared to skin the rat hindlimb. *Neurosci Lett* 52(3):235-240.
7. Mense S (1993) Nociception from skeletal muscle in relation to clinical muscle pain. *Pain* 54(3):241-289.
8. Issberner U, Reeh P W, & Steen K H (1996) Pain due to tissue acidosis: a mechanism for inflammatory and ischemic myalgia? *Neurosci Lett* 208(3):191-194.

9. Molliver D C, et al. (2005) ASIC3, an acid-sensing ion channel, is expressed in metaboreceptive sensory neurons. *Mol Pain* 1:35.
10. Mense S (2008) Muscle pain: mechanisms and clinical significance. *Dtsch Arztebl Int* 105(12):214-219.
11. Immke D C & McCleskey E W (2001) Lactate enhances the acid-sensing Na+ channel on ischemia-sensing neurons. *Nat Neurosci* 4(9):869-870.
12. Birdsong W T, et al. (2010) Sensing muscle ischemia: coincident detection of acid and ATP via interplay of two ion channels. *Neuron* 68(4):739-749.
13. Sluka K A, et al. (2003) Chronic hyperalgesia induced by repeated acid injections in muscle is abolished by the loss of ASIC3, but not ASIC1. *Pain* 106(3):229-239.
14. Sluka K A, Kalra A, & Moore S A (2001) Unilateral intramuscular injections of acidic saline produce a bilateral, long-lasting hyperalgesia. *Muscle Nerve* 24(1):37-46.
15. Sluka K A (2002) Stimulation of deep somatic tissue with capsaicin produces long-lasting mechanical allodynia and heat hypoalgesia that depends on early activation of the cAMP pathway. *J Neurosci* 22(13):5687-5693.
16. Schafers M, Sorkin L S, & Sommer C (2003) Intramuscular injection of tumor necrosis factor-alpha induces muscle hyperalgesia in rats. *Pain* 104(3):579-588.
17. Yen Y T, et al. (2009) Role of acid-sensing ion channel 3 in sub-acute-phase inflammation. *Mol Pain* 5:1.
18. Ambalavanar R, et al. (2006) Deep tissue inflammation upregulates neuropeptides and evokes nociceptive behaviors which are modulated by a neuropeptide antagonist. *Pain* 120(1-2):53-68.
19. Adreani C M & Kaufman M P (1998) Effect of arterial occlusion on responses of group III and IV afferents to dynamic exercise. *J Appl Physiol* 84(6):1827-1833.
20. Taguchi T, Matsuda T, Tamura R, Sato J, & Mizumura K (2005) Muscular mechanical hyperalgesia revealed by behavioural pain test and c-Fos expression in the spinal dorsal horn after eccentric contraction in rats. *J Physiol* 564(Pt 1):259-268.
21. Sluka K A, et al. (2007) ASIC3 in muscle mediates mechanical, but not heat, hyperalgesia associated with muscle inflammation. *Pain* 129(1-2):102-112.
22. Deval E, et al. (2010) Acid-sensing ion channels (ASICs): pharmacology and implication in pain. *Pharmacol Ther* 128(3):549-558.
23. Walder R Y, et al. (2010) *ASIC*1 and ASIC3 play different roles in the development of Hyperalgesia after inflammatory muscle injury. *J Pain* 11(3):210-218.
24. Gandhi R, Ryals J M, & Wright D E (2004) Neurotrophin-3 reverses chronic mechanical hyperalgesia induced by intramuscular acid injection. *J Neurosci* 24(42):9405-9413.
25. Nielsen A N, Mathiesen C, & Blackburn-Munro G (2004) Pharmacological characterisation of acid-induced muscle allodynia in rats. *Eur J Pharmacol* 487(1-3):93-103.
26. Yokoyama T, Maeda Y, Audette K M, & Sluka K A (2007) Pregabalin reduces muscle and cutaneous hyperalgesia in two models of chronic muscle pain in rats. *J Pain* 8(5):422-429.
27. Hoheisel U, Unger T, & Mense S (2005) Excitatory and modulatory effects of inflammatory cytokines and neurotrophins on mechanosensitive group I V muscle afferents in the rat. *Pain* 114(1-2):168-176.
28. Mense S (2009) Algesic agents exciting muscle nociceptors. *Exp Brain Res* 196(1):89-100.
29. Voilley N, de Weille J, Mamet J, & Lazdunski M (2001) Nonsteroid anti-inflammatory drugs inhibit both the activity and the inflammation-induced expression of acid-sensing ion channels in nociceptors. *J Neurosci* 21(20): 8026-8033.
30. Lin Y W, et al. (2008) Identification and characterization of a subset of mouse sensory neurons that express acid-sensing ion channel 3. *Neuroscience* 151(2):544-557.
31. Lu B, et al. (2009) Peptide neurotransmitters activate a cation channel complex of NALCN and UNC-80. *Nature* 457(7230):741-744.
32. Jia Z, et al. (2008) Genistein inhibits voltage-gated sodium currents in SCG neurons through protein tyrosine kinase-dependent and kinase-independent mechanisms. *Pflugers Arch* 456(5):857-866.
33. Belevych A E, Warrier S, & Harvey R D (2002) Genistein inhibits cardiac L-type Ca(2+) channel activity by a tyrosine kinase-independent mechanism. *Mol Pharmacol* 62(3):554-565.
34. Neumann S, Doubell T P, Leslie T, & Woolf C J (1996) Inflammatory pain hypersensitivity mediated by phenotypic switch in myelinated primary sensory neurons. *Nature* 384(6607):360-364.
35. Park T J, et al. (2008) Selective inflammatory pain insensitivity in the African naked mole-rat (Heterocephalus glaber). *PLoS Biol* 6(1):e13.
36. Brand A, Smith E S, Lewin G R, & Park T J (2010) Functional Neurokinin and NMDA Receptor Activity in an Animal Naturally Lacking Substance P: The Naked Mole-Rat. *PLoS One* 5(12):e15162.
37. Mantyh P W, et al. (1997) Inhibition of hyperalgesia by ablation of lamina I spinal neurons expressing the substance P receptor. *Science* 278(5336):275-279.
38. Cao Y Q, et al. (1998) Primary afferent tachykinins are required to experience moderate to intense pain. *Nature* 392(6674):390-394.
39. De Felipe C, et al. (1998) Altered nociception, analgesia and aggression in mice lacking the receptor for substance P. *Nature* 392(6674):394-397.
40. Zimmer A, et al. (1998) Hypoalgesia in mice with a targeted deletion of the tachykinin 1 gene. *Proc Natl Acad Sci USA* 95(5):2630-2635.
41. Hill R (2000) NK1 (substance P) receptor antagonists—why are they not analgesic in humans? *Trends Pharmacol Sci* 21(7):244-246.
42. Min M Y, et al. (2008) Physiological and morphological properties of, and effect of substance P on, neurons in the A7 catecholamine cell group in rats. *Neuroscience* 153 (4):1020-1033.
43. Sculptoreanu A & de Groat W C (2007) Neurokinins enhance excitability in capsaicin-responsive DRG neurons. *Exp Neurol* 205(1):92-100.
44. Jafri M S & Weinreich D (1996) Substance P hyperpolarizes vagal sensory neurones of the ferret. *J Physiol* 493 (Pt 1):157-166.
45. Quartara L & Maggi C A (1997) The tachykinin NK1 receptor. Part I: ligands and mechanisms of cellular activation. *Neuropeptides* 31(6):537-563.
46. Ahn M, Beacham D, Westenbroek R E, Scheuer T, & Catterall W A (2007) Regulation of Na(v)1.2 channels by brain-derived neurotrophic factor, TrkB, and associated Fyn kinase. *J Neurosci* 27(43):11533-11542.
47. Iwasaki Y, Gay B, Wada K, & Koizumi S (1998) Association of the Src family tyrosine kinase Fyn with TrkB. *J Neurochem* 71(1):106-111.
48. Murase S, et al. (2010) Bradykinin and nerve growth factor play pivotal roles in muscular mechanical hyperalgesia after exercise (delayed-onset muscle soreness). *J Neurosci* 30(10):3752-3761.
49. Brown D A & Passmore G M (2009) Neural KCNQ (Kv7) channels. *Br J Pharmacol* 156(8):1185-1195.

50. Linley J E, et al. (2008) Inhibition of M current in sensory neurons by exogenous proteases: a signaling pathway mediating inflammatory nociception. *J Neurosci* 28(44):11240-11249.
51. Liu B, et al. (2010) The acute nociceptive signals induced by bradykinin in rat sensory neurons are mediated by inhibition of M-type K+ channels and activation of Ca2+-activated Cl− channels. *J Clin Invest* 120(4): 1240-1252.
52. Stewart J M, et al. (1976) Substance P and analgesia. *Nature* 262(5571):784-785.
53. Frederickson R C, Burgis V, Harrell C E, & Edwards J D (1978) Dual actions of substance P on nociception: possible role of endogenous opioids. *Science* 199(4335): 1359-1362.
54. Oehme P, Hilse H, Morgenstern E, & Gores E (1980) Substance P: does it produce analgesia or hyperalgesia? *Science* 208(4441):305-307.
55. Ferguson S S (2001) Evolving concepts in G protein-coupled receptor endocytosis: the role in receptor desensitization and signaling. *Pharmacol Rev* 53(1):1-24.
56. Chen Y J, Huang C W, Lin C S, Chang W H, & Sun W H (2009) Expression and function of proton-sensing G-protein-coupled receptors in inflammatory pain. *Mol Pain* 5:39.
57. Russell I J (1998) Neurochemical pathogenesis of fibromyalgia. Z Rheumatol 57 Suppl 2:63-66.
58. Shah J P, Phillips T M, Danoff J V, & Gerber L H (2005) An in vivo microanalytical technique for measuring the local biochemical milieu of human skeletal muscle. *J Appl Physiol* 99(5):1977-1984.
59. Reinert A, Kaske A, & Mense S (1998) Inflammation-induced increase in the density of neuropeptide-immunoreactive nerve endings in rat skeletal muscle. *Exp Brain Res* 121(2):174-180.
60. Urban L A & Fox A J (2000) NK1 receptor antagonists—are they really without effect in the pain clinic? *Trends Pharmacol Sci* 21(12):462-464; author reply 465.
61. Rao S G (2009) Current progress in the pharmacological therapy of fibromyalgia. *Expert Opin Investig Drugs* 18(10):1479-1493.
62. Murase K & Randic M (1984) Actions of substance P on rat spinal dorsal horn neurones. *J Physiol* 346:203-217.
63. Chen C C, Zimmer A, Sun W H, Hall J, & Brownstein M J (2002) A role for ASIC3 in the modulation of high-intensity pain stimuli. *Proc Natl Acad Sci USA* 99(13):8992-8997.
64. Hamer P W, McGeachie J M, Davies M J, & Grounds M D (2002) Evans Blue Dye as an in vivo marker of myofibre damage: optimising parameters for detecting initial myofibre membrane permeability. *J Anat* 200(Pt 1):69-79.
65. Cheng C M, et al. (2010) Probing localized neural mechanotransduction through surface-modified elastomeric matrices and electrophysiology. *Nat Protoc* 5(4): 714-724.
66. Nishiyori M, Ueda H (2008) Prolonged gabapentin analgesia in an exppperimental mouse model of fibromyalgia. Mol Pain 4: 52.

What is claimed is:

1. A method for treating fibromyalgia, comprising administering to a subject in need thereof an effective amount of an adenosine analog, wherein the adenosine analog is a compound of Formula (II):

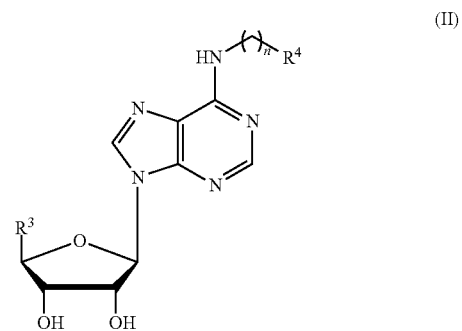

or a pharmaceutically acceptable salt thereof, wherein $R^3$ is hydroxymethyl ($HOCH_2$);

n is 1, 2 or 3; and $R^4$ is an unsubstituted phenyl or a phenyl substituted with a hydroxyl, a halogen group, or both.

2. The method of claim 1, wherein the adenosine analog is T1-11:

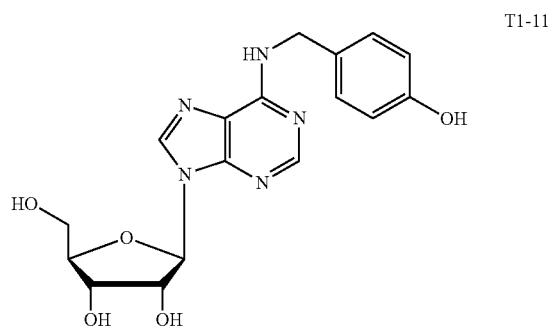

or a pharmaceutically acceptable salt thereof.

3. The method of claim 1, wherein the adenosine analog is JMF1998:

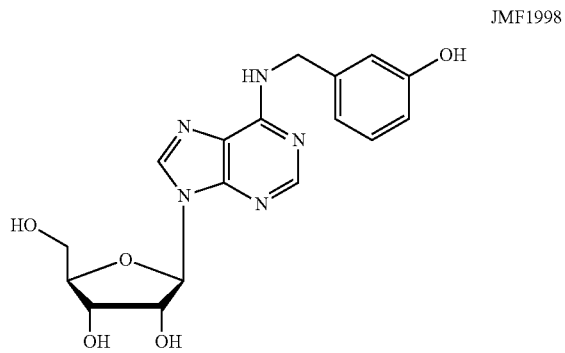

or a pharmaceutically acceptable salt thereof.

4. The method of claim 1, wherein the adenosine analog is JMF2665:

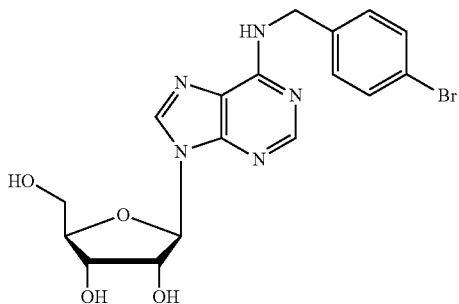

JMF2665 or a pharmaceutically acceptable salt thereof.

5. The method of claim 1 further comprising administering the subject Substance P (SP).

6. A method for treating fibromyalgia, comprising administering to a subject in need thereof an effective amount of an adenosine analog, wherein the adenosine analog is JMF 1907:

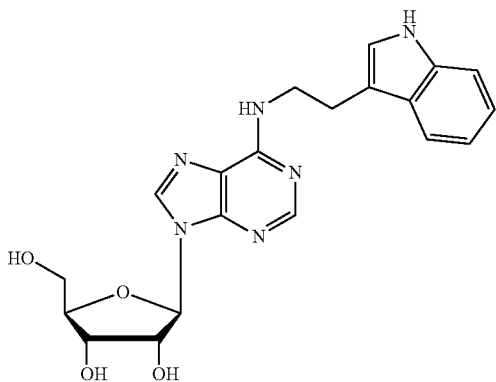

JMF1907 or a pharmaceutically acceptable salt thereof.

7. The method of claim 6, further comprising administering the subject Substance P (SP).

8. A pharmaceutical composition, comprising therapeutically effective amounts of an adenosine analog and Substance P (SP), wherein the adenosine analog is JMF1907 or a compound of Formula (I):

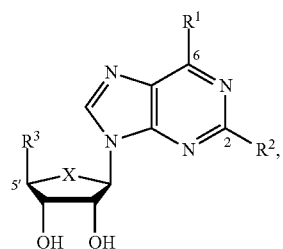

(I)

or a pharmaceutically acceptable salt thereof,
wherein:
X is O;
$R^1$ is —NH(CH$_2$)$_n$R$^4$;
$R^2$ is hydrogen (H);
$R^3$ is hydroxymethyl (HOCH$_2$);
n is 1, 2 or 3; and
$R^4$ is a phenyl and wherein the phenyl is optionally substituted with a hydroxyl, and/or a halogen group, or both.

* * * * *